(12) United States Patent
Monteverde et al.

(10) Patent No.: US 11,419,686 B2
(45) Date of Patent: Aug. 23, 2022

(54) TRAJECTORY REPRESENTATION IN DESIGN AND TESTING OF A SURGICAL ROBOT

(71) Applicant: Verb Surgical Inc., Mountain View, CA (US)

(72) Inventors: David Monteverde, Mountain View, CA (US); Matthew Williams, Mountain View, CA (US); Andrew Bzostek, Mountain View, CA (US)

(73) Assignee: Verb Surgical Inc., Mountain View, CA (US)

( * ) Notice: Subject to any disclaimer, the term of this patent is extended or adjusted under 35 U.S.C. 154(b) by 439 days.

(21) Appl. No.: 16/569,877

(22) Filed: Sep. 13, 2019

(65) Prior Publication Data
US 2021/0077203 A1    Mar. 18, 2021

(51) Int. Cl.
*G05B 19/04* (2006.01)
*G05B 19/18* (2006.01)
(Continued)

(52) U.S. Cl.
CPC ............. *A61B 34/30* (2016.02); *B25J 9/1605* (2013.01); *B25J 9/1633* (2013.01); *B25J 9/1664* (2013.01);
(Continued)

(58) Field of Classification Search
CPC ................... A61B 34/30; A61B 34/37; A61B 2017/00725; A61B 2034/107;
(Continued)

(56) References Cited

U.S. PATENT DOCUMENTS

| 2006/0142656 | A1* | 6/2006 | Malackowski | ........ | A61B 90/36 600/424 |
| 2007/0151389 | A1* | 7/2007 | Prisco | ................... | A61B 34/70 74/490.05 |

(Continued)

OTHER PUBLICATIONS

Title "Mass and Friction Optimization for Natural Motion in Hands-On Robotic Surgery" by Joshua G. Petersen, Stuart A. Bowyer, Member, IEEE, and Ferdinando Rodriguez y Baena, Member, IEEE; IEEE Transactions On Robotics, vol. 32, No. 1, Feb. 2016 (Year: 2016).*

(Continued)

*Primary Examiner* — Abby Y Lin
*Assistant Examiner* — Sohana Tanju Khayer
(74) *Attorney, Agent, or Firm* — Lempia Summerfield Katz LLC

(57) ABSTRACT

For kinetic sizing, the dynamic torque to be provided by a robotic system may be based off of, in part, a maximum acceleration. Rather than trying to extract maximum acceleration from many samples, a relationship of velocity to acceleration from repetitive user inputs relative to a non-surgical target in different situations (e.g., accurate, fast, or balance tracing of the target movement) is established. The velocity for any given situation may be used to estimate the acceleration from the relationship. Rather than using many trajectory samples from many users, a synthetic trajectory may be used. The synthetic trajectory may be fit to user data while maintaining high-coverage properties for direction of movement for any given pose of the robot. Alternatively, a virtual trajectory decoupled from time is used. The virtual trajectory samples the directions at any given pose in a global high-coverage manner, without specifically using a time-dependent sequence of poses.

16 Claims, 10 Drawing Sheets

(51) Int. Cl.
*A61B 34/30* (2016.01)
*B25J 13/06* (2006.01)
*B25J 9/16* (2006.01)
*B25J 19/00* (2006.01)
*A61B 34/37* (2016.01)
*A61B 34/10* (2016.01)
*A61B 17/00* (2006.01)
*A61B 34/20* (2016.01)
*A61B 90/00* (2016.01)

(52) U.S. Cl.
CPC .......... *B25J 9/1679* (2013.01); *B25J 9/1689* (2013.01); *B25J 9/1692* (2013.01); *B25J 13/06* (2013.01); *B25J 19/007* (2013.01); *B25J 19/0095* (2013.01); *A61B 34/37* (2016.02); *A61B 2017/00725* (2013.01); *A61B 2034/107* (2016.02); *A61B 2034/2055* (2016.02); *A61B 2090/066* (2016.02); *A61B 2090/3937* (2016.02)

(58) Field of Classification Search
CPC ...... A61B 2034/2055; A61B 2090/066; A61B 2090/3937; B25J 9/1605; B25J 9/1633; B25J 9/1664; B25J 9/1679; B25J 9/1689; B25J 9/1692; B25J 13/06; B25J 19/007; B25J 19/0095
See application file for complete search history.

(56) References Cited

U.S. PATENT DOCUMENTS

| 2010/0234857 | A1* | 9/2010 | Itkowitz ................. A61B 34/77 606/130 |
| 2017/0049517 | A1* | 2/2017 | Felder .................... A61B 34/30 |
| 2019/0083190 | A1 | 3/2019 | Graves |
| 2019/0206563 | A1* | 7/2019 | Shelton, IV ......... A61B 17/072 |

OTHER PUBLICATIONS

Khatib, Oussama, et al. "Robotics-based synthesis of human motion." Journal of Physiology-Paris 103.3-5 (2009): 211-219.
Vasconcelos, Maria João M., and João Manuel RS Tavares. "Human motion analysis: methodologies and applications." CMBBE 2008 (2008). pp. 1-7.

* cited by examiner

TRAJECTORY REPRESENTATION IN DESIGN AND TESTING OF A SURGICAL ROBOT

BACKGROUND

The present embodiments relate to kinetic (kinematic and dynamic) sizing of robots, such as surgical robots. Minimally-invasive surgery (MIS) may be performed with robotic systems that include one or more robotic arms for manipulating surgical tools based on commands from a remote operator. A robotic arm may, for example, support at its distal end various devices such as surgical end effectors, imaging devices, cannulas for providing access to the patient's body cavity and organs, etc. Using the robotic system, the surgeon directly controls the robotic arms during MIS. This direct control of the robotic arms provides for motion accuracy, dexterity, and allows for presentation of information on a user interface not normally available to the surgeon. However, matching the robotic capabilities to the demands of the user for robotic movement may be difficult. The brakes, transmissions, and motors may be oversized for the likely trajectories, leading to undesired increase in size and cost, or may be undersized, leading to undesired delayed responsiveness in a surgical situation.

The specific robot design and the expected movements of the robot are used to predict static and dynamic torques at robot joints. The expected movements are established from user input in MIS, but different users control the robotic system differently. The expected motion of the robot may be difficult to characterize. Motion logs collected from users performing surgical tasks, such a suturing or knot-tying using either simulators or robots, may provide user input of the trajectories expected of the robotic system, but high and low velocities, frequencies, and accelerations are not easily segregated in terms of relevant situations (e.g., accurate movement versus fast movement). Matching trajectories of movement to sizing of the robot may be difficult. Using one sample of user input of the trajectory may more likely lead to situations where the robot sizing is inappropriate for others. Once sample user inputs for trajectories are identified, accounting for various movement options available may be difficult.

SUMMARY

By way of introduction, the preferred embodiments described below include methods, systems, instructions, and computer readable media for kinetic sizing of a robotic system. The dynamic torque to be provided by the robotic system may be based off of, in part, a maximum acceleration. Rather than trying to extract maximum acceleration from many samples, a relationship of velocity to acceleration from repetitive user inputs relative to a non-surgical target in different situations (e.g., accurate, fast, or balance tracing of the target movement) is established. The velocity for any given situation may be used to estimate the acceleration from the relationship. Rather than using many trajectory samples from many users, a synthetic trajectory may be used. The synthetic trajectory may be fit to user data while maintaining high-coverage properties for direction of movement for any given pose of the robot. Alternatively, a virtual trajectory decoupled from time is used. The virtual trajectory samples the directions at any given pose with high coverage without using the expected direction to the next pose.

Any of the approaches above may be used alone. Any combination of two or more approaches may be used.

In a first aspect, a method is provided for testing a surgical robotic system. User data representing input of movement control over a plurality of trajectories is obtained from a plurality of users. A synthetic trajectory is optimized to the user data. The synthetic trajectory indicating a time history of states of the robotic surgical system. The surgical robotic system is analyzed using inverse kinematics and inverse dynamics from instantaneous output from the synthetic trajectory. Performance of the surgical robotic system is verified from the analyzing.

In a second aspect, a non-transitory computer readable storage medium has stored therein data representing instructions executable by a programmed processor for design or testing of a surgical robot. The storage medium includes instructions for fitting first parameters of a synthetic trajectory to a first frequency, a first velocity, and/or a first acceleration from user input to control the surgical robot; generating a second velocity and/or a second acceleration by the synthetic trajectory with the first parameters as fit to the first frequency, the first velocity, and/or the first acceleration; and determining dynamic torque for a motor of the surgical robot from the second velocity and/or second acceleration.

In a third aspect, a method is provided for parameterizing human motion in a surgical robotic system. A pattern guide at a surgeon counsel of the surgical robotic system is used for tracking motions of a plurality of users tracing the pattern guide in conditions for two different speeds of the tracing. An individual high speed and individual high acceleration for the motions of each of the users for each of the conditions is determined. A population high speed and population high acceleration is determined from the individual high speeds and individual high accelerations for the motion of the users for each of the conditions. A curve is fit to the population high speed and population high acceleration for the conditions. A maximum acceleration is calculated from the curve given a maximum speed. A dynamic torque for a motor of the surgical robot is determined from the maximum speed and the maximum acceleration.

In a fourth aspect, a non-transitory computer readable storage medium has stored therein data representing instructions executable by a programmed processor for design or testing of a surgical robot. The storage medium includes instructions for: determining statistical data from samples of surgical robot control under different operating environments for a population of users; generating a relationship of velocity to acceleration for the surgical robot control over the different operating environments; and determining dynamic torque for the surgical robot from an acceleration determined from the relationship given a velocity of the surgical robot.

In a fifth aspect, a method is provided for generating a virtual trajectory of a surgical robotic system. A plurality of well-spaced directions for velocity and acceleration are defined at each of a plurality of poses of the surgical robotic system. Dynamic torque of the surgical robotic system is determined for each vector combination of the directions for the velocity and the acceleration at each of the poses of the surgical robotic system. A motor of the surgical robotic system is selected based on a maximum one of the dynamic torques over the poses.

In a sixth aspect, a non-transitory computer readable storage medium has stored therein data representing instructions executable by a programmed processor for trajectory representation in a surgical robot. The storage medium includes instructions for: sampling an high-coverage spatial distribution of vector combinations of velocity and acceleration for each of a plurality of poses of the surgical robot; determining dynamic torque of the surgical robotic system for each of the vector combinations at each of the poses of the surgical robotic system; and identifying a maximum of the dynamic torques.

The present invention is defined by the following claims, and nothing in this section should be taken as a limitation on those claims. Any teaching for one type of claim (e.g., method) may be applicable to another type of claim (e.g., computer readable storage medium or system). Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Maximum expected torques are used for sizing brakes, transmissions, and/or motors in quasi-static conditions. The maximum expected torques are used. The maximum torque includes static and dynamic torques. Maximum static torques are either maximum reachable torques in any pose within joint limits of the robot acting against gravity or maximum torques in a surgical pose acting against gravity and tissue loads. Maximum dynamic torques are calculated in operational (e.g., surgical) poses with external loads in various situations. The various situations may be the type or condition of the input, such as accurate or precise guidance of the robot as opposed to fast or more rapid movement where accuracy is not needed. For a surgical robot, the maximum dynamic torque may be determined for any location, such as at a tool shaft end or a joint.

The dynamic torque may be calculated using complex modeling with computationally burdensome simulation. In the embodiments disclosed herein, the dynamic torque is calculated based on instantaneous knowledge of position and motion. An inverse dynamics calculation is used. Various approaches allow for more useful or comprehensive dynamic torque calculation in design and testing. A relationship of velocity to acceleration may be determined based on a study of user input outside of an operational (e.g., surgical) context. The relationship is used to determine instantaneous acceleration given a known velocity, assisting in rapid or more simplified calculation of the dynamic torque. A synthetic trajectory fit to user input from the study with high-coverage (e.g., generally isotropic) directions for velocity and acceleration at each given pose is used to calculate torque without the burden of running many simulations from different users in operational control. Alternatively, a virtual trajectory decoupled from time or change in position is used.

Figure 1:
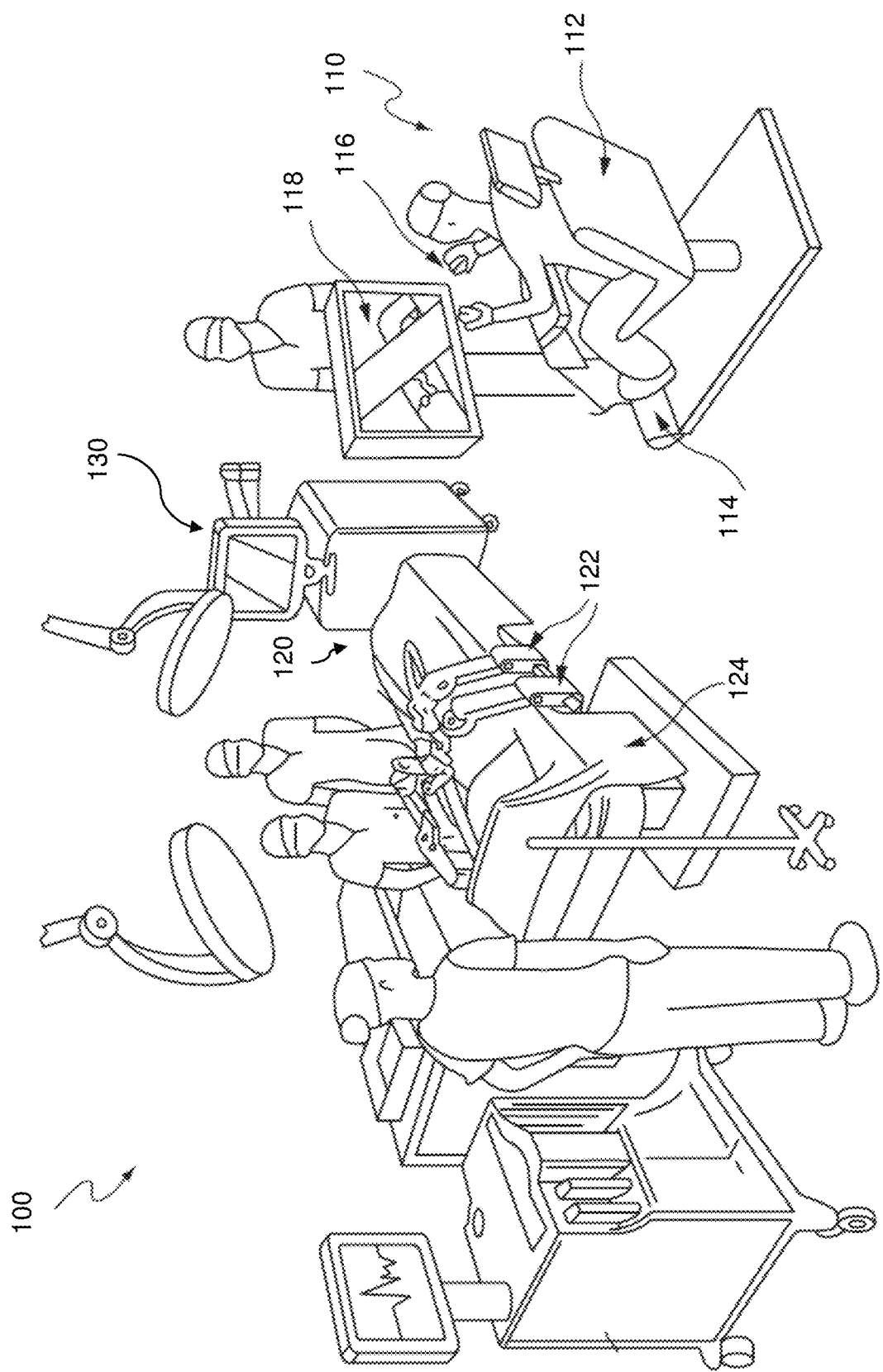
FIG. 1 is an illustration of one embodiment of an operating room environment with a surgical robotic system according to one embodiment.
Figure 2:
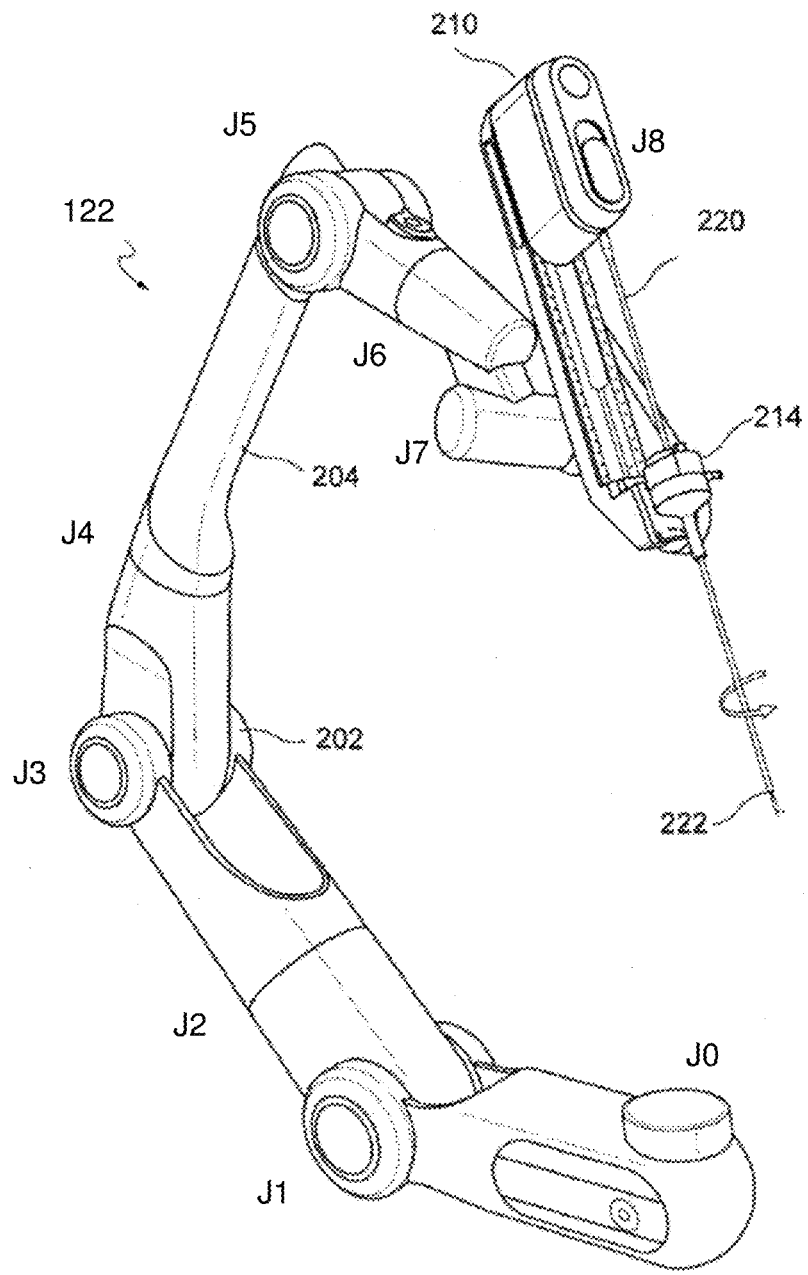
FIG. 2 illustrates an example surgical robot arm.

FIGS. 1 and 2 show an example surgical robotic system. The approaches for assisting in determining dynamic torque are discussed below in reference to this example system. Other surgical robotic systems and surgical robots or non-surgical robotic systems and robots may use the approaches.

Figure 3:
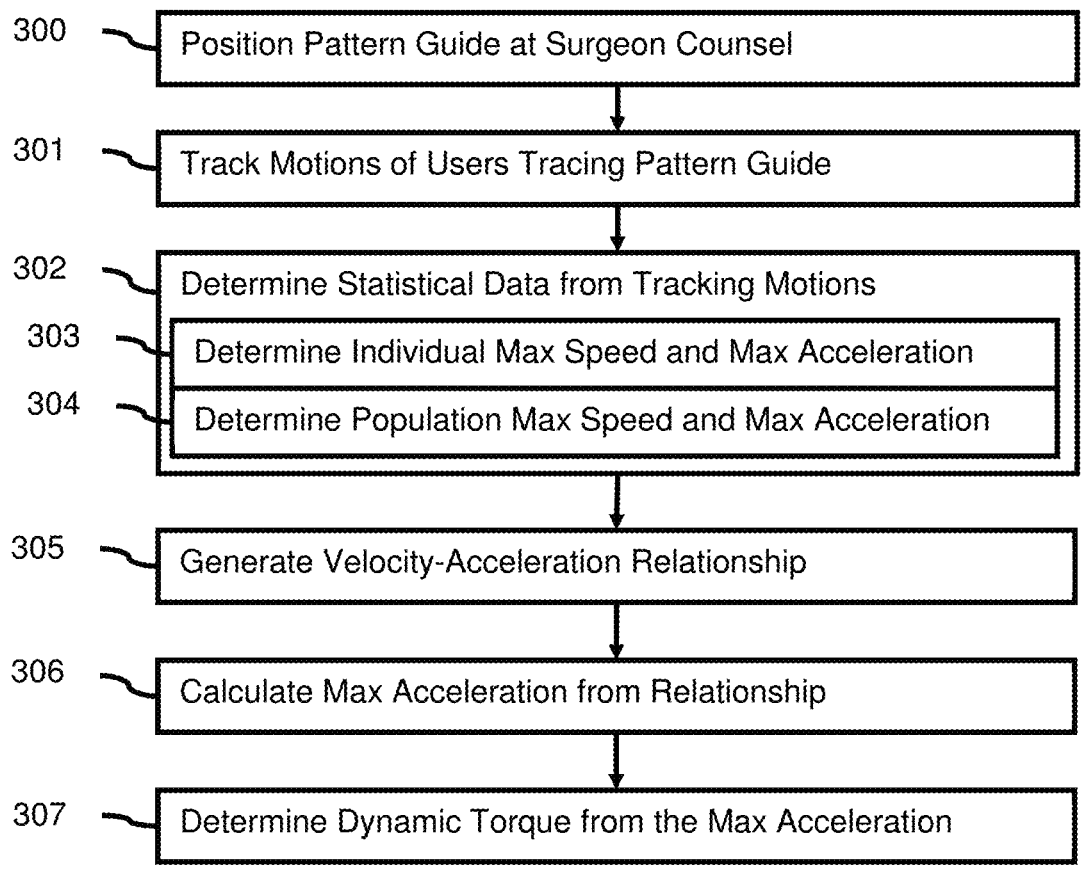
FIG. 3 is a flow chart diagram of one embodiment of a method for generating and using a relationship between velocity and acceleration in user input to control a robotic system.
Figure 4:
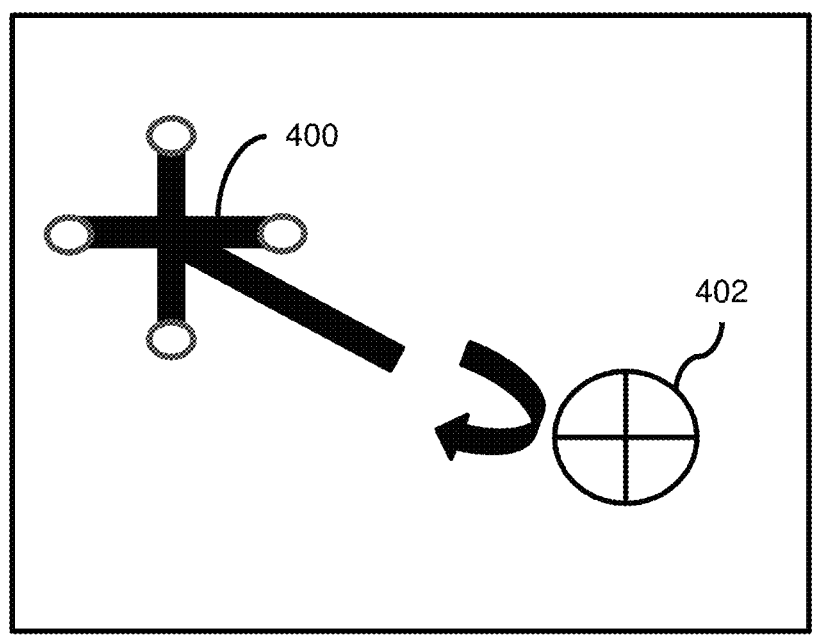
FIG. 4 shows an example arrangement for gathering user data for control of a robotic system.
Figure 5:
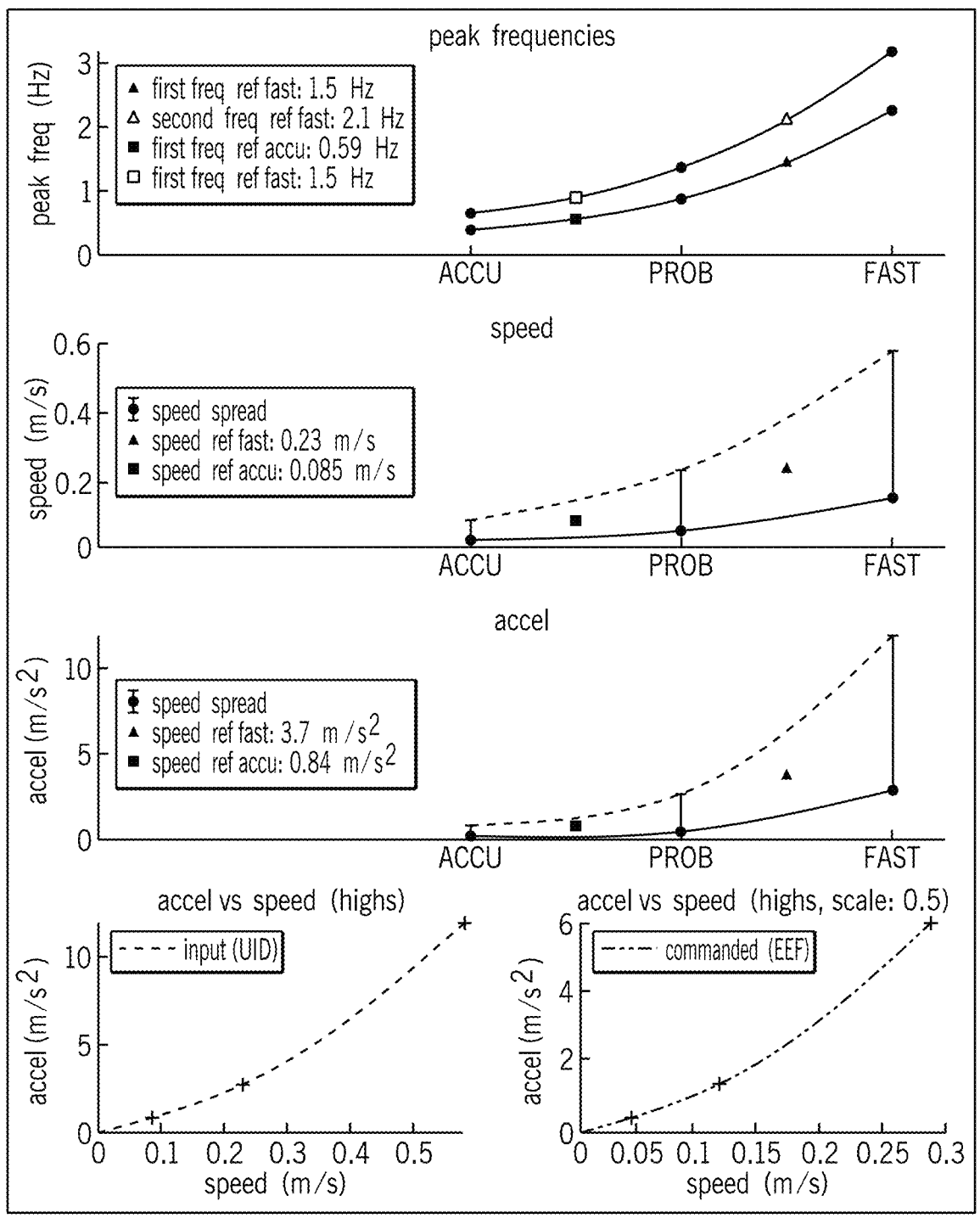
FIG. 5 shows graphs from statistical analysis of user data for control of a robotic system.
Figure 6:
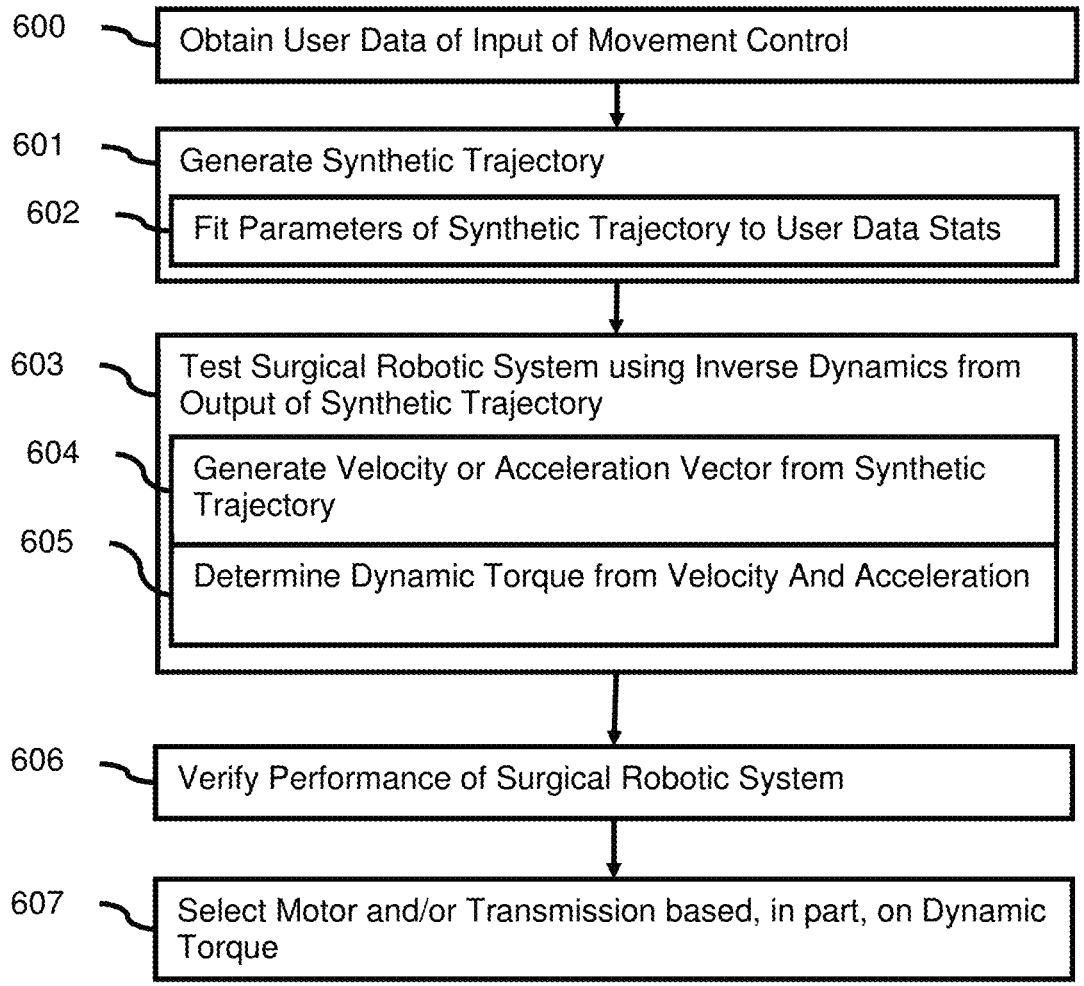
FIG. 6 is a flow chart diagram of one embodiment of a method for generating and using a synthetic trajectory.
Figure 7:
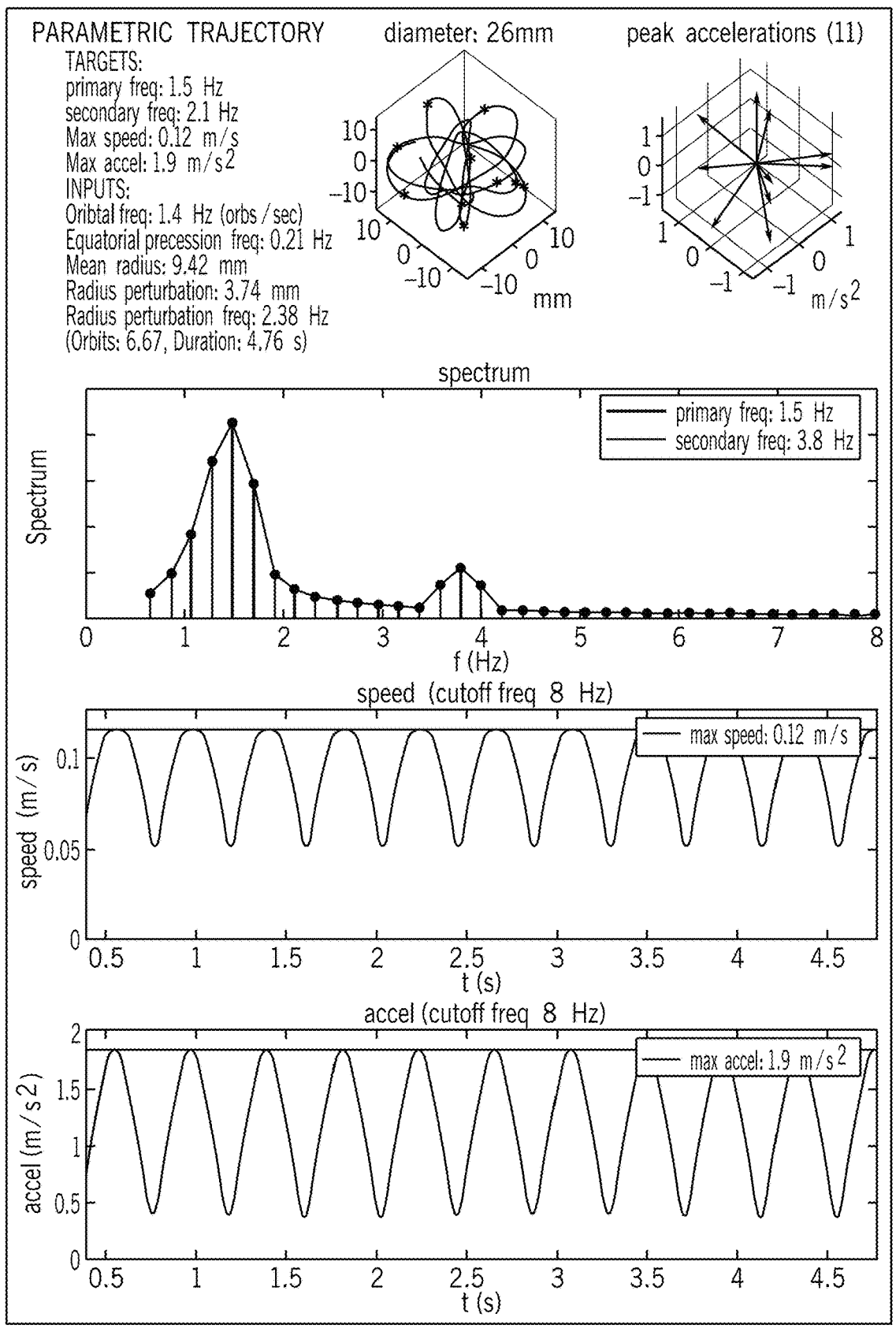
FIG. 7 shows parametric trajectory information for a fit synthetic trajectory.
Figure 8:
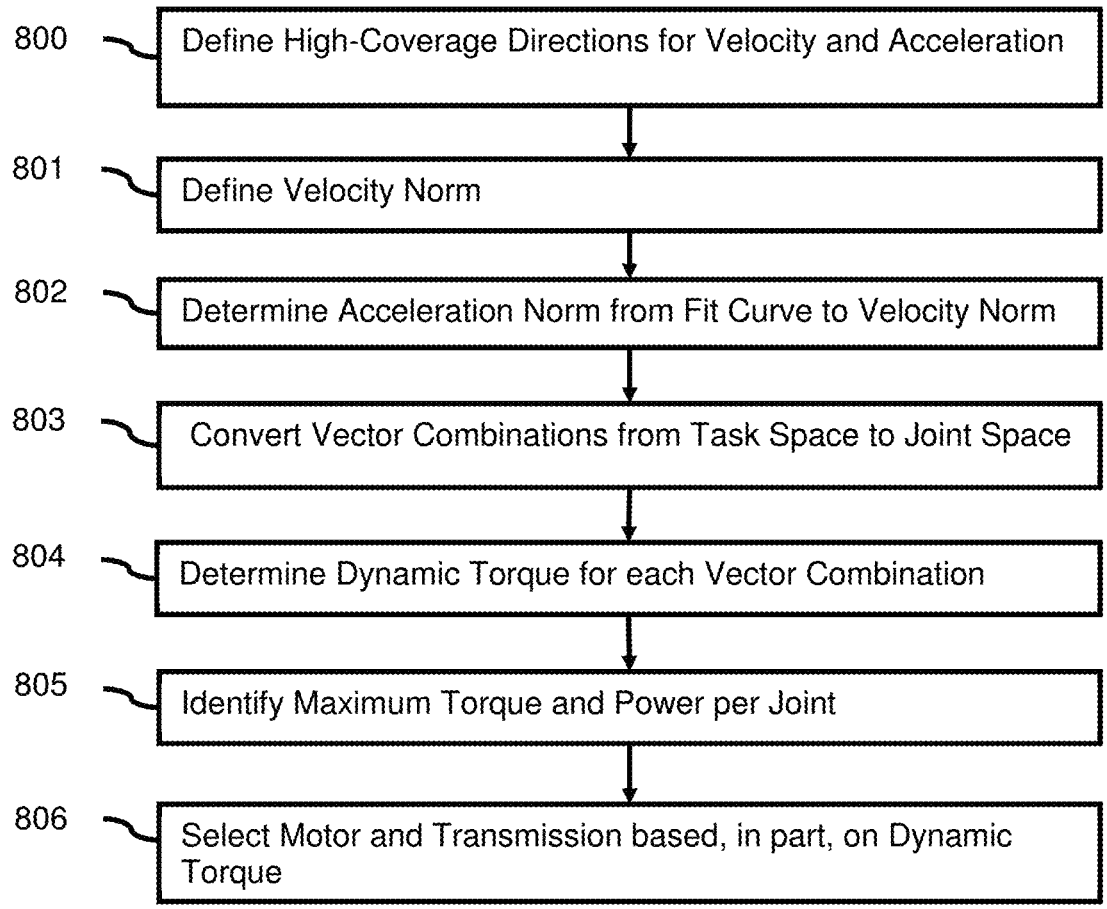
FIG. 8 is a flow chart diagram of one embodiment of a method for generating and using a virtual trajectory.
Figure 9:
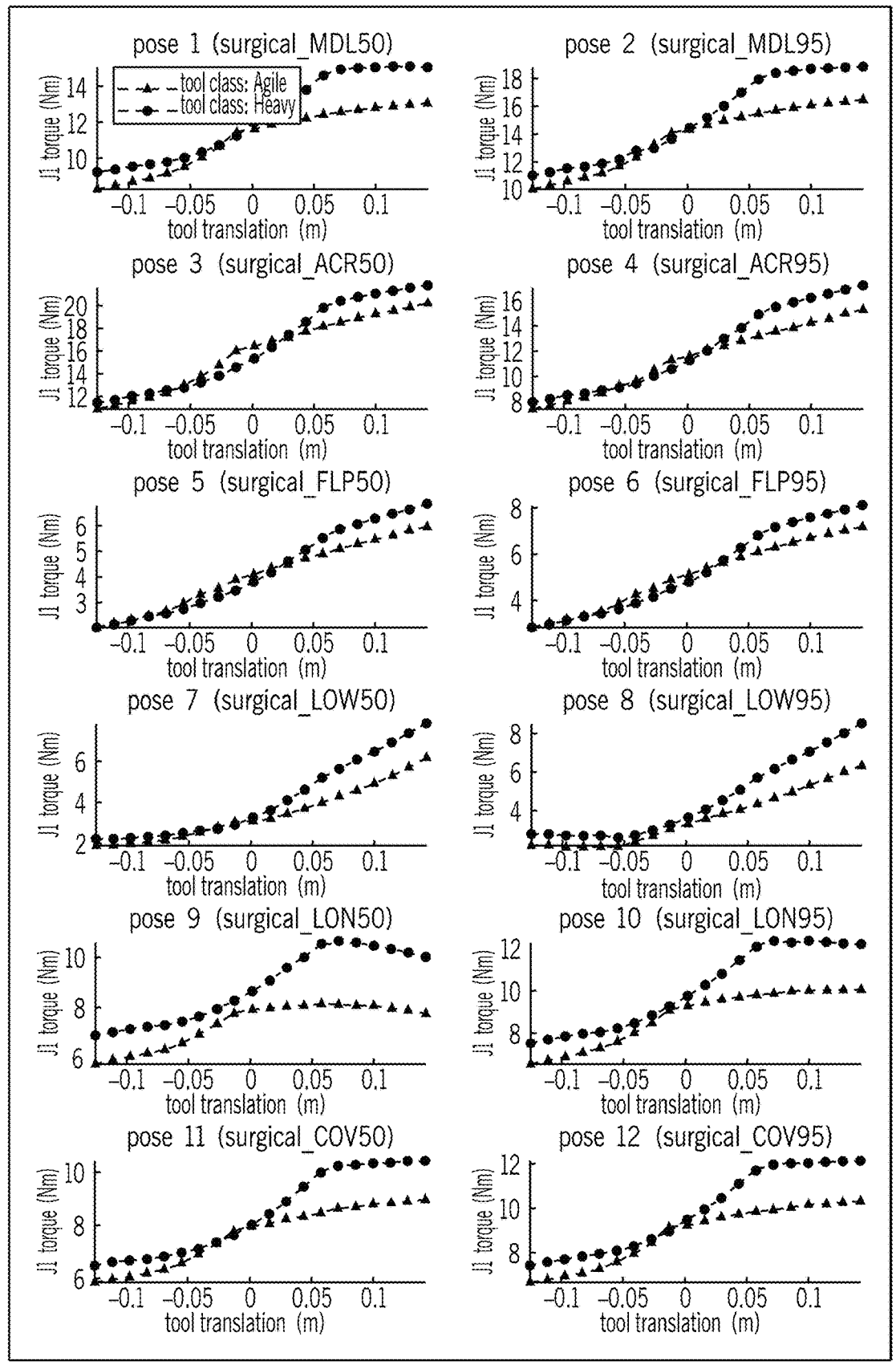
FIG. 9 shows graphs of torque as a function of tool translation of insertion axis for a joint in different poses of the surgical robot of FIG. 2.

FIGS. 3-5 are directed to the first approach where the relationship between velocity and acceleration is determined based on user input relative to a target pattern. FIGS. 6-7 are directed to the second approach where a synthetic trajectory is generated for dynamic torque, such as for testing a robotic system. FIGS. 8-9 are directed to the third approach where a virtual trajectory is used instead of the synthetic trajectory, such as for sizing.

FIG. 1 is a diagram illustrating an example operating room environment with a surgical robotic system 100 for which the motors, transmissions, and/or brakes are to be sized or tested for operation under expected dynamic torque. The surgical robotic system 100 includes a user console 110, a control tower 130, and a surgical robot 120 having one or more surgical robotic arms 122 mounted on a surgical platform 124 (e.g., a table or a bed etc.), where surgical tools with end effectors are attached to the distal ends of the robotic arms 122 for executing a surgical procedure. Additional, different, or fewer components may be provided, such as combining the control tower 130 with the console 110 or surgical robot 120. The robotic arms 122 are shown as table-mounted, but in other configurations, the robotic arms 122 may be mounted in a cart, a ceiling, a sidewall, or other suitable support surfaces.

Generally, a user, such as a surgeon or other operator, may be seated at the user console 110 to remotely manipulate the robotic arms 122 and/or surgical instruments (e.g., teleoperation). The user console 110 may be located in the same operation room as the robotic system 100, as shown in FIG. 1. In other environments, the user console 110 may be located in an adjacent or nearby room, or tele-operated from a remote location in a different building, city, or country. The user console 110 may comprise a seat 112, pedals 114, one or more handheld user interface devices (UIDs) 116, and an open display 118 configured to display, for example, a view of the surgical site inside a patient and graphic user interface for selecting, programming, and using task templates. As shown in the exemplary user console 110, a surgeon sitting in the seat 112 and viewing the open display 118 may manipulate the pedals 114 and/or handheld user interface devices 116 to remotely and directly control the robotic arms 122 and/or surgical instruments mounted to the distal ends of the arms 122. This user control determines the rate and change in rate of movement of the robotic arms 122. The rate and change in rate result in dynamic torque expected to be provided by the robotic arms 122. The surgeon sitting in the seat 112 may view and interact with the display 118 for using task templates for automation of operation of the robotic arms 122 and/or surgical instruments in the surgery.

In some variations, a user may also operate the surgical robotic system 100 in an "over the bed" (OTB) mode, in which the user is at the patient's side and simultaneously manipulating a robotically-driven tool/end effector attached thereto (e.g., with a handheld user interface device 116 held in one hand) and a manual laparoscopic tool. For example, the user's left hand may be manipulating a handheld user interface device 116 to control a robotic surgical component while the user's right hand may be manipulating a manual laparoscopic tool. Thus, in these variations, the user may perform both robotic-assisted MIS and manual laparoscopic surgery on a patient.

During an exemplary procedure or surgery, the patient is prepped and draped in a sterile fashion to achieve anesthesia. Initial access to the surgical site may be performed manually with the robotic system 100 in a stowed configuration or withdrawn configuration to facilitate access to the surgical site. Once the access is completed, initial positioning and/or preparation of the robotic system may be performed. During the procedure, a surgeon in the user console 110 may utilize the pedals 114 and/or user interface devices 116 to manipulate various end effectors and/or imaging systems to perform the surgery. The movements may be surgeon, patient, and/or situation specific, so may vary. Manual assistance may also be provided at the procedure table by sterile-gowned personnel, who may perform tasks including but not limited to, retracting tissues or performing manual repositioning or tool exchange involving one or more robotic arms 122. Some surgical tasks, such as retracting, suturing, or other tissue manipulation, may instead be performed by one or more robotic arms 122 (e.g., third or fourth arms). Nonsterile personnel may also be present to assist the surgeon at the user console 110. When the procedure or surgery is completed, the robotic system 100 and/or user console 110 may be configured or set in a state to facilitate one or more post-operative procedures, including but not limited to, robotic system 100 cleaning and/or sterilization, and/or healthcare record entry or printout, whether electronic or hard copy, such as via the user console 110.

In some aspects, the communication between the surgical robot 120 and the user console 110 may be through the control tower 130, which may translate user input from the user console 110 to robotic control commands and transmit the control commands to the surgical robot 120. The control tower 130 may also transmit status and feedback from the robot 120 back to the user console 110. The connections between the surgical robot 120, the user console 110, and the control tower 130 may be via wired and/or wireless connections and may be proprietary and/or performed using any of a variety of data communication protocols. Any wired connections may be optionally built into the floor and/or walls or ceiling of the operating room. The surgical robotic system 100 may provide video output to one or more displays, including displays within the operating room, as well as remote displays accessible via the Internet or other networks. The video output or feed may also be encrypted to ensure privacy and all or portions of the video output may be saved to a server or electronic healthcare record system.

Prior to initiating surgery with the surgical robotic system, the surgical team can perform the preoperative setup. During the preoperative setup, the main components of the surgical robotic system (e.g., table 124 and robotic arms 122, control tower 130, and user console 110) are positioned in the operating room, connected, and powered on. The table 124 and robotic arms 122 may be in a fully-stowed configuration with the arms 122 under the table 124 for storage and/or transportation purposes. The surgical team can extend the arms 122 from their stowed position for sterile draping. After draping, the arms 122 can be partially retracted until needed for use. A number of conventional laparoscopic steps may need to be performed including trocar placement and insufflation. For example, each sleeve can be inserted with the aid of an obturator, into a small incision and through the body wall. The sleeve and obturator allow optical entry for visualization of tissue layers during insertion to minimize risk of injury during placement. The endoscope is typically placed first to provide hand-held camera visualization for placement of other trocars. After insufflation, if required, manual instruments can be inserted through the sleeve to perform any laparoscopic steps by hand.

Next, the surgical team may position the robotic arms 122 over the patient and attach each arm 122 to a corresponding sleeve. The surgical robotic system 100 has the capability to uniquely identify each tool (endoscope and surgical instruments) upon attachment and display the tool type and arm location on the open or immersive display 118 at the user console 110 and the touchscreen display on the control tower 130. The corresponding tool functions are enabled and can be activated using the master UIDs 116 and foot pedals 114. The patient-side assistant can attach and detach the tools, as required, throughout the procedure. The surgeon seated at the user console 110 can begin to perform surgery using the tools controlled by two master UIDs 116 and foot pedals 114. The system translates the surgeon's hand, wrist, and finger movements through the master UIDs 116 into precise real-time movements of the surgical tools. Therefore in direct teleoperation, the system constantly monitors every surgical maneuver of the surgeon and pauses instrument movement if the system is unable to precisely mirror the surgeon's hand motions. In case the endoscope is moved from one arm to another during surgery, the system can adjust the master UIDs 116 for instrument alignment and continue instrument control and motion. The foot pedals 114 may be used to activate various system modes, such as endoscope control and various instrument functions including monopolar and bipolar cautery, without involving surgeon's hands removed from the master UIDs 116.

FIG. 2 is a schematic diagram illustrating one exemplary design of a robotic arm, a tool drive, and a cannula loaded with a robotic surgical tool, in accordance with aspects of the subject technology. As shown in FIG. 2, the example surgical robotic arm 122 may include a plurality of links (e.g., a link 202) and a plurality of actuated joint modules (e.g., a joint 204, see also joints J1-8) for actuating the plurality of links relative to one another. The joint modules may include various types, such as a pitch joint or a roll joint, which may substantially constrain the movement of the adjacent links around certain axes relative to others. Also shown in the exemplary design of FIG. 2 is a tool drive 210 attached to the distal end of the robotic arm 122. The tool drive 210 may include a cannula 214 coupled to its end to receive and guide a surgical instrument 220 (e.g., endoscopes, staplers, etc.). The surgical instrument (or "tool") 220 may include an end effector 222 at the distal end of the tool. The plurality of the joint modules of the robotic arm 122 can be actuated to position and orient the tool drive 210, which actuates the end effector 222 for robotic surgeries. The end effector 222 is at a tool shaft end. In other embodiments, the tool shaft end is a tip of a needle or other object.

In the example of FIG. 2, the joint J0 is a table pivot joint and resides under the surgical table top. Joint J0 is nominally held in place during surgery. Joints J1 to J5 form a setup or Cartesian arm and are nominally held in place during surgery, so do not contribute to dynamic torque during surgical operation. Joints J0 to J5 experience dynamic reaction torques as a result of motion in joints J6, J7 and J8. Joints J6 and J7 form a spherical arm that may actively move during surgery or teleoperation. Joint J8 translates the tool 220, such as the end effector 222, as part of a tool driver. Joint J8 may actively move during surgery. Joints J6-8 actively position a tool shaft end (i.e., end effector 222) during surgery while maintaining an entry point into the patient at a fixed or stable location (i.e., remote center of motion) to avoid stress on the skin of the patient. During set-up, any of the joints J0-J8 may move, so may be subject to dynamic torque. During surgery, the joints J6-8 are subject to dynamic torque under the influence of the user control or teleoperation. The teleoperation and corresponding dynamic torques may vary from user-to-user due to the differences in situation (e.g., different patients, different pathology, different temperatures, different purposes, and/or different time constraints) and/or user input (e.g., different conditions for control, such as fast movement, accurate or slow movement, or any balance between the two).

FIG. 3 is a flow chart diagram of one embodiment of a method for parameterizing human motion in a surgical robotic system. To determine dynamic torque, a pose of the surgical robot arm 122, including a translation position of the end effector 122 (i.e., pose of the joint J8), and a speed at the tool shaft end (i.e., end effector 122) are established. To calculate torque using inverse dynamics, an acceleration is needed. The level of acceleration for a given speed is not known a-priori. A relationship between velocity and acceleration is determined for different situations for control of the robot arm 122.

Motion logs collected from users performing surgical tasks, such a suturing or knot-tying using either simulators or the robot arm 122, may be examined to find the acceleration. However, high and low velocities and accelerations are not easily segregated in terms of relevant phases or user input conditions (e.g., accurate, fast, or balanced input). FIG. 3 is directed to a simplified yet more comprehensive manner to determine the relationship. Target pattern tracing rather than actual surgical operation is used to characterize parameters of interest in human motion as relevant to robotic surgery.

The method of FIG. 3 is implemented by a computer, such as a personal computer or server. A computer of the surgical robotic system 100 may be used. A physical target and motion sensing system (e.g., stereo camera) are used to gather data with or without corresponding movement of the robot arm or arms 112.

The acts are performed in the order shown or other orders. Additional, different, or fewer acts may be used. For example, acts 303 and 304 are not performed. As another example, acts 306 and/or 307 are not performed. In yet another example, the velocity-acceleration relationship is used for other purposes, such as finding a velocity from a known or input acceleration.

In act 300, a pattern guide is positioned at a surgeon counsel 110 of the surgical robotic system 100. The pattern guide may be positioned at other locations, such as at a desk. The pattern guide is positioned relative to a user for tracing the pattern as if operating the UID 116 of the surgical robotic system 100. The pattern guide is fixed or releasably connected to hold the pattern guide in position, such as a bendable support structure that clamps on one end and holds the pattern guide on the other end.

Any pattern guide may be used. FIG. 4 shows an example. The pattern guide 402 is a circle enclosing cross hairs. This pattern provides for both curved motion and linear motions in different directions. Other example patterns include oblong or "S" curve shapes. Any shape may be used. The shape may direct motion along shapes or partial trajectories likely to be used in control of the surgical robot arm 122.

The pattern guide 402 is sized based on typical input for operation of the robot arm 122. For example, the circle of the pattern guide 402 has a 30 mm diameter. Larger or smaller pattern guides 402 may be used.

In act 301, motions of a plurality of users tracing the pattern guide 402 are tracked in conditions for two or more different speeds of the tracing. Only one speed of tracing may be used in other embodiments.

A user is positioned (e.g., seated or standing) relative to the pattern guide 402, such seating the user at a surgeon console 110. In preparation for data collection, the user sits down at the surgeon console 110 and is asked to arrange armrests and the trajectory pattern guide 402 in comfortable positions.

The subject then follows or traces the trajectory patterns of the pattern guide 402. In the example pattern guide 402 of FIG. 4, the user traces around the circle and traces along each line of the cross-hair.

The motion is tracked using a sensor. For example, the user holds a device, such as a pen or a UID 116. A magnetic position sensor and/or inertial measurement unit may be used to determine position and/or change in position of the pen or UID 116 during tracing. As another example, the user holds a marker 400 with a structure allowing for visual tracking, such as optical patterns or structures on one or more parts of the marker 400 (e.g., balls on ends of a cross extending from the user's hand). A stereo camera and/or depth camera tracks the motion of the marker 400 as the user traces the pattern guide 402. Using known geometric relationship of parts of the marker 400, the location of the pen tip is tracked in two or three dimensions by the camera.

One user may not adequately represent input motion for controlling the robot arm 122. Motion tracking is performed for multiple users. For example, motions for 5, 7, 10, or more users are tracked. Users of any skill level may be tracked, such as tracking some users (e.g., 3) with greater experience in surgical robot manipulation and other users (e.g., 4) with less or no experience in surgical robot manipulation.

Motion tracking may be performed for a single condition or different conditions. In one embodiment, the different conditions correspond to different movement circumstances or goals. For example, two or more conditions from a range of fast to accurate tracing are used. The speed and/or accuracy are used as conditions. The users may be asked to trace the pattern guide 402 quickly as one condition, accurately (e.g., more slowly) as another condition, and a balance between speed and accuracy as a third condition. In other embodiments, the different conditions correspond to different environments (e.g., high temperature, noisy, and/or stressed) or another difference that may affect motion of the user in control of a robotic arm 122.

In the example used herein, the motion tracking is performed for each user under three different contextual conditions: accurate, likely or probable (e.g., balance between fast and accurate), and fast. For example, each user is instructed to make circular motions following the circle in the pattern guide 402, under three different contextual conditions (i.e., three separate trials) where condition 1 is optimizing for accuracy ("accurate"), condition 2 is balancing speed and accuracy ("probable"), and condition 3 is as fast as possible ("fast"). The users are also instructed to make back-and-forth linear motions following the vertical line in the pattern guide 402 for the same three conditions. The users are also instructed to make back-and-forth linear motions following the horizontal line in the pattern guide 402 for the same three conditions. Given the three patterns (e.g., circle, vertical line, horizontal line) and the three conditions (e.g., accurate, probable, fast), user data from tracking seven users is provided for 63 trials.

In alternative embodiments, user data for control for surgical use or surgical simulation is gathered. As the user or users operate the surgical robot arm 122, the motion of the user to control the robot arm 122 is tracked. Tracking following the pattern guide 402 may provide more consistent data for developing a relationship between velocity and acceleration in user input.

In act 302 of FIG. 3, statistical data is determined from the tracked motions. For example, the samples of robot control under different operating environments for a population of users is used to determine statistical data. Motion or tracking data for different operating environments, such as different speed and/or accuracy conditions, is used. Alternatively, the statistical data is determined for one condition.

By tracking data for different users, a population-based representation of motion in control of a robot may be generated. Statistics from a population may more accurately and/or broadly represent the user input motions likely to occur. In act 303, individual statistics are determined. In act 304, population statistics are determined from the individual statistics. In other embodiments, population statistics are determined from the user data for motion input without determining individual statistics.

The statistics are for any parameter or characterization of motion. For example, velocity and acceleration statistics are determined. Other statistics may or may not be determined, such as the frequency. For frequency, the motion data is converted to a frequency domain by a fast Fourier transform. The first or primary frequency of the first or greatest peak in the spectrum is determined. A second or secondary frequency for the second or next highest peak may be determined. The frequency statistics may indicate reliability of the user data.

In act 303, a processor determines an individual high speed and an individual high acceleration for the motions of each of the users for each of the conditions. High speed and high acceleration are in reference to the mean or a lower speed and lower acceleration. For example, the high speed and high acceleration are higher than the means by 1, 2, or 3 standard deviations (e.g., mean speed plus 3 sigma). These high speeds and accelerations may represent the likely or probable extremes in speed and acceleration in the input by the user. Other speed or acceleration may be used, such as determining the mean or low (e.g., value at 1, 2, or 3 standard deviations below the mean).

In one embodiment, a first level of data analysis and extraction is performed for each user given a particular contextual condition. With three conditions and seven users, 21 subject-level analyses are performed. The following statistics are determined: mean speed, mean+$3^{rd}$ sigma speed, mean acceleration, mean+3 sigma acceleration, and first two peak frequencies. Additional, different, or fewer statistics may be determined for each user.

In act 304, a processor determines a population high speed and population high acceleration from the individual high speeds and individual high accelerations for the motion of the users for each of the conditions. Other speed and/or acceleration statistics may be determined, such as the population mean speed and population mean acceleration. Frequency statistics for the population may be determined, such as the mean frequency for the first and second peaks of the individual mean frequencies for the first and second peaks.

In one embodiment, the population high speed is determined as a value at a standard deviation above the mean of the individual high speeds (i.e., mean of individual high speeds plus 1 sigma). Other deviations or a mean of the individual high values without adding deviation may be used. The population high acceleration is also determined as a mean of the individual high accelerations plus 1 sigma.

The population statistics provide for motion information across a range of users. This second level of data analysis and extraction is performed for each of the 3 contextual conditions (accurate, probable, fast) based on the 21 subject-level analyses. This second level analysis is representative of the population. In one embodiment, the determined statistics include: mean of individual means for speed and acceleration. To capture "likely maximum values" for the population, a mean+$1^{st}$ sigma of the individual subjects [mean+$3^{rd}$ sigma] values is calculated for each of speed and acceleration. For frequencies, the means of mean frequencies for the first and second peaks are calculated.

FIG. 5 shows an example of the population statistics. The top three graphs show population statistics across the three conditions. Curves are fit to the determined statistics. Values in-between the conditions are extracted based on the fit curves. The top graph is for the population first and second peak frequencies where the lower line is for the frequency at the first peak. The second graph is for the speed. The dashed line is the maximum speed calculated as the mean of the individual high speeds (+$3^{rd}$ sigma) plus $1^{st}$ sigma. The solid line is the population mean. The third graph is for the acceleration. The dashed line is the maximum acceleration calculated as the mean of the individual high accelerations (+3sigma) plus 1 sigma. The solid line is the population mean.

In act 305 of FIG. 3, the processor generates a relationship of velocity to acceleration for the surgical robot control over the different operating environments. For example, the relationship of high or maximum velocity to high or maximum acceleration across the conditions is determined.

In one embodiment, the relationship is represented as a curve. The curve is fit to the velocity and acceleration. Velocity is graphed along one dimension, such an X-axis, and acceleration is graphed along another dimension, such as a Y-axis. The pairs of velocity and acceleration from each of the conditions (e.g., operating environments) are plotted. Using those point with or without the origin (i.e., known accurate zero velocity and zero acceleration), the curve is fit.

Any curve fitting may be used. For example, a least squares difference or regression is applied to fit a second order polynomial or exponential to the points. Interpolation or other fitting may be used. Lines, third order polynomials, or other functions for the curvature may be used.

In the example of FIG. 5, the processor fits a curve to the population high speed and population high acceleration for each of the three conditions (e.g., fast, probable, and accurate) and the origin. The bottom-left graph shows a dotted line as the fit curve to the three points ("+") and the origin. For accurate conditions, a "high speed" and a "high acceleration" defines one coordinate, a different "high speed" and corresponding "high acceleration" defines another coordinate for probable, and yet another high speed and high acceleration defines another coordinate for fast motion condition. Thus, the bottom-left graph shows a relationship between "likely maximum speed" and "likely maximum acceleration" over a range of speeds and accelerations.

This relationship is deduced from direct hand motion. This corresponds to speeds and accelerations of the "master" in a master-slave robotic control. The relationship may be determined for the resulting motion of the end effector 222 or other part of the robot arm 122. For example, the relationship is to be used to determine the acceleration of the tool shaft end (e.g., end effector 222). The acceleration of the input motion to control may be converted, or the relationship may be converted. FIG. 5 shows an example conversion of the relationship. Motion at the UID 116 is typically scaled to the end-effector 222 or other tool shaft end using factors between 0.5 and 0.2. The scale factor used, a likely scale factor, or the worst-case scale factor (e.g., 0.5) is used for conversion. Using the selected scale factor, the curve is converted from the input motion or UID space to the robot arm, task, or tool shaft end space. The bottom-right graph of FIG. 5 shows the example relationship or curve of the bottom-left graph after conversion. This relationship may be used to calculate a "likely maximum/high acceleration" given a "likely maximum/high speed" at the tool shaft end.

In act 306 of FIG. 3, the processor calculates a maximum acceleration from the curve given a maximum speed. The relationship allows determination of an acceleration given any velocity. The relationship may be represented by the curve, a look-up table, or a function. Given an input velocity, an acceleration is output.

The robot may undergo any trajectory in operation. By determining the speed of part of the robot (e.g., end effector), the acceleration may be determined based on the population statistics.

In act 307, the processor determines a dynamic torque for the surgical robot from an acceleration determined from the relationship given a velocity of the surgical robot. Inverse dynamics is used. For an instant in time, the pose and velocity are known. The relationship from act 305 is used to determine the acceleration in act 306. Once acceleration, pose, and velocity are known at the end effector 222, inverse kinematics calculations result in angular speeds and accelerations at the robot joints. These are used together with mass properties of the robot to calculate torques at the robot joints, using inverse dynamics formulations.

The dynamic torque, plus any static torque, may be used to determine a motor, transmission, and/or brake to use for the surgical robot. The dynamic torque for any joint may be determined from the dynamic torque for the tool shaft end. The brake, transmission, and/or motor may be sized based on the dynamic torque. In the robot arm 122, the sizing provides brakes, motors, and transmissions that are likely to responsively operate over a range of operating conditions. For example, the maximum speed is used to determine a maximum acceleration so that the sizing is for the maximum dynamic torque.

The velocity and pose used in calculating the dynamic torque may be based on a trajectory of motion of the end effector 222 or other part of the robot arm 122. The trajectory may be an actual trajectory, such as measured or sensed during actual use. Alternatively, the trajectory is a synthetic trajectory created with desired limitations through optimization (see FIG. 6) or a virtual trajectory created without consideration for change over time (see FIG. 8) (e.g., performing inverse dynamic calculations at arbitrary directions for the maximum speed or another speed and the maximum acceleration or another acceleration at a pose of the surgical robot).

FIG. 6 is a flow chart diagram of one embodiment of a method for generating and using a synthetic trajectory for a surgical robotic system (e.g., for testing). Rather than using trajectories from movement during surgery, a synthetic trajectory is generated. The synthetic trajectory represents motion the robot arm could take but not necessarily motion that the robot arm was actually controlled to take. By generating a synthetic trajectory, the trajectory may be limited. For example, the trajectory may be limited to be high-coverage so that any dynamic torque calculated from the synthetic trajectory more likely covers or represents the range of possible motions. The synthetic trajectory is an idealized trajectory broadly representative of intended motions of end-effectors. The idealized synthetic trajectories are used for design, testing, and/or analysis of a robotic system, as well as to set representative conditions in system and subsystem requirements.

The method of FIG. 6 is implemented by a computer, such as a personal computer or server. A computer of the surgical robotic system 100 may be used. The surgical robotic system may be used in testing by following the synthetic trajectory. Simulation may be used.

The acts are performed in the order shown or other orders. Additional, different, or fewer acts may be used. For example, act 606 is performed as part of act 603. As another example, acts 603-606 and/or act 607 are not performed. Act 607 may be part of design of the surgical robot, and acts 603-606 may be part of testing of a designed surgical robot.

In act 600, user data representing input of movement control over a plurality of trajectories is obtained from a plurality of users. A database of user data is accessed. Alternatively, the user data is collected by tracking. The user data provides various trajectories for control of the robotic arm.

The user data represents human motion for different conditions (e.g., different rates of movement). For example, user data for control directed to accurate, fast, and a balance between accurate and fast is acquired. Motion trajectories at different rates are obtained.

The user data is for motion using an untethered or wireless UID 116. This wireless controller allows for freedom of movement and corresponding trajectories in three spatial dimensions. In other embodiments, a tethered user interface device is used. Alternatively, a joystick or other user input device with a more limited spatial range of motion may be used.

In one embodiment, acts 300 and 301 of FIG. 3 are performed to obtain the user data. The user data includes trajectories from tracing a target while tracking the tracing or user motion. Alternatively, the user data is from actual control during surgery or surgical simulation. Motion logs collected from users performing surgical tasks, such a suturing or knot-tying using either simulators or prototype robots, may be used.

In act 601, a processor generates a synthetic trajectory. The synthetic trajectory is optimized to the obtained user data. The optimized or fit synthetic trajectory may be used to indicate an instantaneous state of the robotic surgical system (e.g., robot arm 122 or end effector 222), such as providing a velocity, acceleration, and pose in three dimensions. The velocity and acceleration from the relationship of act 305 of FIG. 3 may be absolute values or magnitudes, so do not include directional information. The synthetic trajectory may be used to indicate the direction of the speed and direction of the acceleration.

The synthetic trajectory is a real trajectory but not necessary one that would be used in operation or control of the robot for its intended purpose. Instead, the synthetic trajectory is generated to exhibit desired characteristics, such as targeted maximum speeds, accelerations and frequencies, while providing desired limitations, such as isotropy. The directions for the velocity or acceleration provided by the synthetic trajectory are high-coverage. If vector directions are modeled as points on the surface of a unit sphere, "high coverage" avoids large regions on this surface that are left unpopulated, providing a low "coverage gap" of points on the unit sphere. The coverage gap is a largest angle between any (arbitrary) direction vector and a direction vector contained in the set under consideration. The set under consideration is composed by all acceleration vectors contained in the trajectory. For example, a coverage gap of 15 degrees means that given any arbitrary direction of acceleration vector, the trajectory has an acceleration vector that is within 15 degrees of it. Obtaining a high coverage means making the coverage gap small. A reasonable quantification of "small" makes use of the Platonic Solid with the largest number of vertices, the dodecahecron. The dodecahedron has 20 vertices that are very well distributed in terms of coverage gap. The coverage gap for the dodecahedron is 33 degrees. High coverage is provided where the coverage gap is 33 degrees or below.

A trajectory paradigm that exhibits high directional coverage is capable of being tuned to mimic key characteristics of human motion. The parametric trajectory is based on resolved human motion input parameters by fitting to control motion trajectories while still maintaining high directional coverage. The synthetic trajectory may be tunable following "Axiomatic Design," minimize information content, maintain independence of functional requirements, and/or have a "Design Matrix" as close as possible to diagonal (uncoupled design) or triangular (decoupled design).

In act 602, parameters of the synthetic trajectory are fit to characteristics of the trajectories of the obtained user data. Any characteristics of the user motion may be used, such as the first and/or second peak frequency, velocity, and/or acceleration. For example, the characteristics are the ones provided in the top three graphs of FIG. 5.

The synthetic trajectory is parameterized. One or more variables may be set to fit the synthetic trajectory to provide the characteristics. In one embodiment, the synthetic trajectory is an orbital-type trajectory, such as associated with low earth orbit or other orbits of satellites or celestial bodies. The orbital-type trajectory may be parameterized by radius, orbital frequency, equatorial precession frequency, perturbation of the radius, and perturbation frequency. Additional, different, or fewer parameters may be used, such as where the radius is fixed. Other trajectories having regular motion with substantial high-coverage amongst possible velocity and/or acceleration directions may be used. Substantial provides for 5 degrees of variation from the high-coverage angle of 33 degrees. The synthetic trajectory is different than any or most user entered trajectories.

To have the high-coverage distribution of acceleration and/or velocity directions, the orbital trajectory is defined to have an equatorial precession. The expressions describing the synthetic trajectory can be tuned to exhibit the same basic kinematic characteristics (e.g., in terms of frequencies, speeds and accelerations) observed in intentional human motion, such as captured by the tracking tracing of a target.

This synthetic trajectory is designed to exhibit a high level of directional coverage. In one embodiment, the rotation matrix is parameterized by natural invariants. The rotation axis vector is assumed to be normalized.

n2Q::usage="Qn2Q[n] Transformation from natural invariants to rotation matrix. The input rotation axis must be in normalized form.

Input:n={θ, k1, k2, k3}, where θ is rotation angle (in radians) and k is rotation vector (norm must be 1).

Output: Q=rotation matrix (3×3)";

n2Q[n_]:=Module[{θ, k, k1, k2, k3},

θ=n[[1]];

k=n[[{2,3,4}]];

(*k=k/Norm[k]*)

k1=k[[1]];

k2=k[[2]];

k3=k[[3]];

$k1^2+\text{Cos}[\theta]-k1^2 \text{Cos}[\theta]$ $k1k2-k1k2 \text{Cos}[\theta]-k3 \text{Sin}[\theta]$
$k1k3-k1k3 \text{Cos}[\theta]+k2 \text{Sin}[\theta](k1k2-k1k2 \text{Cos}[\theta]+k3 \text{Sin}[\theta]$
$k2^2+\text{Cos}[\theta]-k2^2 \text{Cos}[\theta]$ $k2k3-k2k3 \text{Cos}[\theta]-k1 \text{Sin}[\theta])]$
$k1k3-k1k3 \text{Cos}[\theta]-k2 \text{Sin}[\theta]$ $k2k3-k2k3 \text{Cos}[\theta]+k1 \text{Sin}[\theta]$
$k3^2+\text{Cos}[\theta]-k3^2 \text{Cos}[\theta]$ The trajectory is tunable via the parameters in such a way that desired frequency content, maximum speeds and/or maximum accelerations may be obtained. One key property of this orbit is that it exhibits a high-coverage of linear acceleration directions. For high directional coverage, a fixed polar axis kPolar is defined to point along the Z axis:

kPolar={0,0,1};

The equatorial axis kEquat is defined to be contained within the equatorial (X-Y) plane and rotates about axis kPolar at an angular speed wEquatInst. If the initial state of the equatorial axis is kEquat0 (initial state aligned with the X axis), then kEquat as a function of time is:

kEquat0={1,0,0};

rotNatInvEquat=Join[{2 π fEquat t},kPolar];

kEquat=n2Q[rotNatInvEquat].kEquat0

{Cos[2 fEquatπt], Sin[2fEquatπt], 0}

A position of interest (say, for a tool tip) may be described with a vector rPos, which has an initial state rPos0 that points along the Z axis. If the instantaneous norm (length) of this position vector is ri, then:

rPos0={0,0, ri};

If rPos is obtained by rotating rPos0 about the instantaneous equatorial axis kEquat at an orbital frequency fOrb, then it holds that:

rotNatInvOrb=Join[{2 π fOrb t},kEquat];

rPos=n2Q[rotNatInvOrb].rPos0

{ri Sin[2fEquatπt]Sin[2fOrbπt], −ri Cos[2 fEquatπt] Sin[2 fOrbπt], ri Cos[2fOrbπt]}

The value of ri is specified as a function of time. If r is the mean orbit radius, perturbed by rPert at a frequency fPert, then amplitude ri (of the rotating vector) is:

ri=r+rPert Sin[2πfrPertt];

And so rPos is, explicitly:

rPos//MatrixForm

Sin[2fEquatπt]Sin[2fOrbπt](r+rPert Sin[2frPertπt])

(−Cos [2 fEquatra]Sin[2 fOrbπt](r+rPert Sin[2frPertπt]))

Cos[2fOrbπt](r+rPert Sin[2frPertπt])

The final design synthesized from this effort results in the following expression: "[sin(2.*fEquat.*pi.*t).*sin (2.*fOrb.*pi.*t).*(r+rPert.*sin(2.* . . . \n frPert.*pi.*t)), (−1).*cos(2.*fEquat.*pi.*t).*sin(2.*fOrb.*pi.*t).* . . . \n (r+rPert.*sin(2.*frPert.*pi.*t)), cos(2.*fOrb.*pi.*t).*(r+ rPert.* . . . \n sin(2.*frPert.* pi.*t))];". This expression may be used as the synthetic trajectory. Other expressions may be used.

The result is a synthetic trajectory with high-coverage distribution of the velocity and acceleration directions but without being an actual trajectory entered by the user. In fitting to the user data, the values of the parameters of the synthetic trajectory are set so that the synthetic trajectory generates values of the characteristics provided by the user data. The first and/or second peak frequency, velocity, and/or acceleration generated by the synthetic trajectory are to match the first and/or second peak frequency, velocity, and/or acceleration from the user data (i.e., of the motion to control the robotic arm 122). The orbital-type trajectory is fit to emulate or generate the desired motion characteristics, such as characteristics derived from multiple users or a population of users.

In one embodiment, the orbital frequency is coupled to the primary frequency (e.g., first peak of the power spectrum of the motion in the frequency domain), the reference radius is coupled to the maximum speed, the radius perturbation is coupled to the maximum acceleration, the radius perturbation frequency is coupled to the secondary frequency (e.g., second peak of the power spectrum), and the equatorial precession frequency is coupled to the isotropy.

Optimization is applied to fit the synthetic trajectory to the characteristics derived from the user motion. A specific instantiation of the synthetic trajectory depends on five quantities: orbital frequency, equatorial precession frequency, reference radius, radius perturbation and radius perturbation frequency. These five quantities are used as optimization parameters (driving parameters) to obtain an instantiation of the synthetic trajectory that possesses desired characteristics such as primary frequency, secondary frequency, maximum speed and maximum acceleration. These four quantities are targets or objectives. In one embodiment, a desired set (e.g., four) of target quantities is obtained using a combination of non-linear optimization and heuristics. The objective (cost) function for the optimization is Cartesian distance (in four-dimensional space) between the target vector (user data statistics) and state vector (synthetic trajectory generated statistics). Specifically:

objective_function=(freq_primary_target−freq_primary)^2+ . . . .

(freq_secondary_target−freq_secondary)^2+ . . . .

(speed_max_target−speed_max))^2+ . . . .

(accel_max_target−accel_max))^2;

where {freq_primary, freq_secondary, speed_max, accel_max} is the state vector. Other optimizations may be used. The heuristics provide for manual interference to avoid false minimum or maxima in the optimization. Other guidance may be provided.

The optimization matches the synthetic trajectory to the user data without being an actual trajectory represented in the user data. To match the characteristics of frequency, velocity, and acceleration (e.g., a primary frequency and a secondary frequency, a maximum velocity, and a maximum acceleration), a cost function that includes these characteristics is used. The values of the parameters of the synthetic trajectory are adjusted during optimization based on feedback or differentials from the cost function. Any cost function may be used, such as the Cartesian distances, average distances, or a weighted average distance.

FIG. 7 shows an example of the synthesized trajectory optimized to the user data represented in FIG. 5. FIG. 7 shows the motion parameters and general forms of the optimized synthetic trajectory. The user data from the fast motion for the control condition is used. The fast trajectory represents fairly aggressive motion, potentially expected during tasks such as fast tissue dissection where accuracy is less important. On the other hand, the accurate trajectory represents motion during tasks that require higher levels of accuracy, such as positioning a needle. The specific trajectory is achieved via a combination of numerical optimization routines and educated guesses (i.e., human acumen). The top graphs show the orbits of the synthetic trajectory and the spatial vectors of the peak acceleration.

The trajectories are resolved at the robot end-effector by applying a scale factor of 0.5 between the UID 116 and end-effector 222. The maximum target speeds and accelerations are scaled accordingly from those shown in FIG. 7, which are the motions at the UID 222. The target and achieved parameters for both fast and accurate trajectories are shown in Tables 1 and 2:

TABLE 1

| Metric | Target (Goal) | | Achieved | |
|---|---|---|---|---|
| Primary freq | 1.5 Hz | | 1.5 Hz | |
| Secondary freq | 2.1 Hz | | 3.8 Hz | |
| Max speed | 0.12 m/s | | 0.12 m/s | |
| Max accel | 1.9 m/s2 | | 1.9 m/s2 | |
| Coverage gap | <33 deg | | 15 deg | |

TABLE 2

| Metric | Target (Goal) | | Achieved | |
|---|---|---|---|---|
| Primary freq | 0.59 Hz | | 0.59 Hz | |
| Secondary freq | 0.93 Hz | | 1 Hz | |
| Max speed | 0.043 m/s | | 0.043 m/s | |
| Max accel | 0.42 m/s2 | | 0.42 m/s2 | |
| Coverage gap | <33 deg | | 9 deg | |

The synthesizing of the trajectories in terms of reflecting targeted motion parameters matches the characteristics well. For both fast and accurate conditions, 4 out of 5 parameter targets are achieved, while one parameter (secondary frequency) was slightly higher than targeted. Since the synthetic trajectory is formed for providing the vector or spatial angle information in calculating dynamic torque, the secondary frequency being close but not exact is acceptable.

The synthetic trajectory captures motion characteristics present in a population of users, as opposed to a single user, by being optimized to the statistical characteristics from the population. The high level of directional coverage (coverage gap at 9 and 15 degrees) brings the complexity and number of potential tests to manageable levels when used in setting and verification of requirements. For a given pose, multiple directions may be sampled. The synthetic trajectory samples the directions with high coverage or substantially high-coverage.

In act 603 of FIG. 6, the surgical robotic system is tested using inverse kinematics from the synthetic trajectory. The testing is based on joint-level time histories of pose, velocity, and acceleration. For example, a starting pose is set by modeling or the user. The velocity is a maximum velocity allowable to prevent risk of serious injury to any person hit by the robotic arm. The acceleration is a maximum acceleration determined from the relationship between velocity and acceleration. The directions of velocity and acceleration are from the synthetic trajectory. Different directions defined by the synthetic trajectory may be tested for any given pose. By modeling the operation of the robotic surgical system moving along the synthetic trajectory, dynamic torques are provided.

In act 604, the processor generates a velocity and/or an acceleration as vectors using the fit or optimized synthetic trajectory, such as the trajectory optimized to provide the primary and secondary frequencies, the maximum velocity, and/or the maximum acceleration. The velocity and/or acceleration as vectors are generated as an instantaneous state of the surgical robot arm. The synthetic trajectory outputs the vector or vectors for a given time.

In act 605, the processor determines the dynamic torque or power from the instantaneous output. The state in the form of the vector or vectors at a given time is used to determine the dynamic torque using inverse dynamics.

The dynamic torque is determined for the end effector 222. The dynamic torque may be determined for any joint undergoing movement. The modeling of the robotic arm is used to determine the movement of a joint given the movement of the end effector 222. The dynamic torque of the end effector 222 is used to determine the dynamic torque of the joint based on the relative motion. The motor power to provide the dynamic torque may be calculated.

The dynamic torque is expressed in joint space. The dynamic torques may be mapped to motor space using a transmission ratio and estimates for joint efficiency.

The testing models performance of motors, transmissions, and/or brakes. The determined dynamic torque is applied to test for sufficiency in the motors, transmissions, and/or brakes for one or more joints. By determining the dynamic torque with inverse dynamics from the instantaneous state provided by the synthetic trajectory, the operation of the robotic arm is tested.

In act 606, the performance of the surgical robotic system (e.g., robotic arm) is verified from the testing. Where the motor, brake, and/or transmission is capable of providing the maximum dynamic torque expected, the performance is verified. Since the dynamic torque is based on expected forms of control motions and sampled over a high-coverage distribution of spatial vectors along a trajectory based on population information, the verification likely covers all or most expected operation of the robotic arm. The transmission, motor, and brake sizes are verified as capable of operation in the synthetic trajectory. The verification may be performed by modeling, avoiding a trial-and-error approach. Alternatively, the verification is performed after or as part of selection of act 607. In act 607, a motor, transmission, or brake are selected. Rather than testing or as a result of failure of verification, the determination of dynamic torque may be used to design the robotic arm. The size of the motor, brake, and/or transmission are selected based on the maximum dynamic torque for the joint. The selection is based on the joint power (torque and speed).

FIG. 8 shows one embodiment of a flow chart of a method for generating a virtual trajectory (e.g., quasi-trajectory) of a surgical robotic system. As an alternative to generating the synthetic trajectory or using an actual trajectory, the virtual trajectory is used. Since inverse dynamics may be used, the trajectory as an actual path of motion is not needed. The virtual trajectory provides instantaneous state without providing a path or change as a function of time.

The method is implemented by a processor, such as a computer or server. A robotic arm and/or corresponding model may be used for some acts.

The acts are performed in the order shown or a different order. For example, act 803 may be performed before or after any of acts 800 and 802. Additional, different, or fewer acts may be provided. For example, act 805 and/or act 803 are not performed. As another example, acts for determining power and/or for transmission or brake selection are provided. In yet another example, act 802 is not performed where the directions are defined in the desired space.

In act 800, the processor samples a high-coverage spatial distribution of vector combinations of velocity and acceleration for each of a plurality of poses of the surgical robot. The virtual trajectory or sampling provides the spatial or direction information. For calculation of dynamic torque from inverse dynamics, the pose specified by the operation of the robotic arm 122 including the translation of the end effector 222 over a range, the speed (e.g., maximum speed) of the end effector 222 based on safety or other considerations, and the acceleration (e.g., maximum acceleration) based on the relationship of velocity to acceleration are used. As discussed above for the synthetic trajectory, the direction of the velocity and acceleration are used. The speed and acceleration are absolute values (a single number for each). To solve the inverse dynamics, spatial vectors are used for these quantities.

For synthetic trajectory, the fit trajectory along which the robot may actually move provides the directions. An actual trajectory during operation of the robot may be used, but risks lack of representation of other possible motions. In this "virtual" embodiment, a virtual trajectory or instantaneous state without a physical trajectory (i.e., without change in position over time) provides the directions. The tool shaft end (e.g., end effector 222) is treated as having different combinations of directions for velocity and acceleration vectors at any given pose. A direction is chosen for velocity and a different or same direction is chosen for the acceleration in that instant. Other directions may be sampled for that instant. The inverse dynamics calculations for that instant are performed for each combination of velocity and acceleration vectors.

The sampling of different vector directions or combinations for each instant emulates a set of trajectories, all of which pass through the tool shaft end. Each of these trajectories has a different combination of velocity and acceleration directions at that point. These different trajectories are, in fact, physically realizable. Rather than using the physically realizable trajectories, the directions are sampled for the instant without coupling to time. For example, two vectors (velocity and acceleration) are bound to the same point and must be co-planar. If a trajectory that is a planar circle and the speed is constant around the circle, then the acceleration is perpendicular to the velocity vector. If the speed is changing but the trajectory remains circular, then the velocity and acceleration vectors are no longer perpendicular but can be made to have an almost arbitrary angle between them. Finally, for a straight trajectory, velocity and acceleration vectors that are parallel (either in the same or in opposite directions) result. A hypothesis of different combinations of directions for velocity and acceleration vectors is reasonable and represents various possible trajectories for any given instant without needing the trajectories.

The directions are defined for any number of different poses and/or instants. For example, a set of 12 reference surgical poses are provided for the robotic arm 122 of FIG. 2. Joints J0-J5 are fixed or held steady for each pose, while joints J6-8 may move dynamically. The 12 different poses are for joints J0-J5 or joints J0-J7 and provide an envelope that covers the surgical procedures designated for the surgical robotic system 100. Different poses for different times may be provided for joints J6-8. Alternatively, the set of reference poses are for joints J0-J7 as fixed and the translation of Joint J8 is sampled at different positions any number of times, such as 20 different positions over the range of possible positions.

For each instant or pose, any number of vector combinations may be sampled. For example, 200 or more vector combinations are sampled. As another example, ten or more directions are defined in three dimensions. These ten or more directions for velocity and acceleration provide for 100 or more vector combinations for the directions. In one embodiment, 20 directions spaced around a sphere are defined to generate combinations of speed and velocity vectors. This gives 400 sets of velocity-acceleration vector combinations for each pose. This array of 400 combinations is analogous to 400 actual trajectories, except that the pose remains constant and the change from one pose to the next and corresponding change in combination vector is decoupled from time.

If 20 poses covering the effective range of tool translation of joint J8 while holding joints J0-J7 in one position, a total of 8000 sampled configurations are provided per surgical pose. For all 12 surgical poses, a total of 96000 sets of joint torques may be determined. The sampling may be done for different tools, such as for two different tools. For two tools, 192,000 sets of dynamic joint torques may be obtained.

Since sampling over pre-defined directions for each instant or pose is used, the directions may be defined to have a desired characteristic, such as high coverage or substantially high-coverage.

In one embodiment, evenly spaced directions to provide high coverage are defined and used for sampling directions. The directions are used to determine dynamic torque with inverse dynamics, so a change in time is not needed. The directions are defined free of consideration of a trajectory of the surgical robotic system or robotic arm or arms. Inverse dynamics does not need an actual trajectory to be solved. Inverse dynamics uses pose, velocity, and acceleration at a given instant. The virtual trajectory approach takes advantage of that fact to cut out use of a trajectory. The directions are defined, and inverse dynamics used decoupled from time.

In act 802, the processor determines an acceleration. For example, a maximum acceleration is determined. In one embodiment, the acceleration is determined from a curve fit to statistical data from tracings of a target by multiple users. For example, the relationship determined in act 305 of FIG. 3 is used to generate the maximum acceleration in act 306 of FIG. 3 from an input velocity, such as the maximum velocity determined in act 801.

In act 801, the maximum velocity may be a default value, based on study, or from another source. In one embodiment, the maximum velocity is a speed limit constraining movement of the robot arm 122. The maximum allowable speed for the tool shaft end or end effector is determined by safety considerations of the patient and/or people or objects adjacent to the robot arm 122. In one embodiment, the speed limit is based on the notion that for an accidental contact scenario between a robot and an operator, a certain amount of kinetic energy is fully deposited into the affected body region of the operator. Maximum permissible energy transfer is based on the lowest energy transfer that could result in a minor injury, such as a bruise. For the side or back of the head, the maximum permissible energy transfer corresponding to the skull and forehead is 0.23 Joules, to limit the possibility of a concussion. An absolute speed limit applicable to any robot part that could potentially come in contact with the head of a surgical staff member is calculated. For the robot arm 122 of FIG. 2 and within a range of tool masses, the speed limit is ~0.5 m/s. The same speed limit is used for each direction of motion, but different speed limits may be used for different directions.

The absolute speed limit is converted to a speed limit at the tool shaft end. For the robot arm 122 of FIG. 2, the speed limit may be calculated on a plane of motion for Joint J7. The speed at the tool shaft end and the stationary location at the remote center of motion (i.e., entry into the skin of the patient) are used to determine the speed contribution from different joints J6-8. The speed at the tool shaft end is a minimum of the speeds of the Joints J6-8. Other maximum velocity determinations may be used.

The directions for velocity and acceleration vectors are defined at the tool shaft end at different instants. Let us call the velocity and acceleration vectors at a given instant $\dot{x}$ and $\ddot{x}$. To execute the inverse dynamics calculations, the vector combinations are converted from the tool shaft end space to joint space in act 803 using inverse kinematics. In one embodiment, the baseline inverse dynamics algorithm uses pose, velocity and acceleration inputs in joint space $(q, \dot{q}, \ddot{q})$ for the joints of the robot arm. The velocity and acceleration inputs in task space ($\dot{x}$ and $\ddot{x}$) for operation of the robot arm are converted to joint space for operation of the joints. The conversion is from the dynamics of the tool shaft end to the dynamics of the joints.

Any conversion of velocity from task space to joint space may be used. For example, a Jacobian matrix is used, as represented by:

$$\dot{x}=J(q)\dot{q}$$

where $q=(q6, q7, q8)$ for joints J6-8 is a 3×3 square matrix. Solving for $\dot{q}$, the representation becomes:

$$\dot{q}=J^{-1}(q)\dot{x}.$$

For acceleration, the representation is differentiated with respect to time, as represented by:

$$\ddot{q}=\dot{J}^{-1}(q)\dot{x}+J^{-1}(q)\ddot{x}.$$

A first order approximation of the time derivative $J^{-1}(q)$ is obtained from:

$$\dot{J}^{-1}(q) \approx \frac{J^{-1}(q_+) - J^{-1}(q)}{\delta t},$$

where $q_+=q+\dot{q}\delta t$ for suitably small $\delta t$. $\dot{q}$ and $\ddot{q}$ may thus be determined from $\dot{x}$ and $\ddot{x}$. Other conversions may be used. The inverse dynamics may be used to obtain joint dynamic torques based on this conversion.

In act 804 of FIG. 8, the processor determines a dynamic torque of the surgical robotic system. The dynamic torque is determined for each vector combination of velocity and acceleration as defined by the virtual trajectory (e.g., each maximum speed and maximum acceleration vector). The dynamic torques are determined for each of the poses, such as each translational position of the end effector 222 due to translation by the joint J8 for each of the 12 different poses of the robotic arm 122.

The dynamic torque is determined from inverse dynamics. The pose, velocity vector (direction and magnitude), and acceleration vector (direction and magnitude) are used to inversely determine the dynamic torque. Since many samples of directions are used, the dynamic torque for each direction possibility is determined. The maximum of the dynamic torques across poses is selected so that the size of the brake, transmission, and/or motor satisfies the need represented by the maximum dynamic torque. Alternatively, a mean or any deviation from mean other than the maximum may be selected.

Where the dynamic torque is determined in the tool shaft end or task space, the dynamic torque may be converted to dynamic torques of joints in joint space. The dynamic torques for each of all or a sub-set of joints (e.g., J6-8) are determined for sizing.

FIG. 9 shows example dynamic torques for joint J1 in 12 different poses, where the complete pose is represented by 20 different tool translation positions (i.e., translations by joint J8). Each pose graph includes the dynamic torque determined for each of the complete poses (i.e., translation positions for the given pose of the rest of the joints J0-J7).

In act 805, the maximum dynamic torque and power per joint across poses is selected. For example, the maximum torque in all of the graphs of FIG. 9 is selected for joint J1. The maximum dynamic torque of all these poses is selected. Alternatively, a mean of the maximums or mean plus 1 sigma is selected. The maximum power is determined from the dynamic torque and speed for each joint.

In act 806, a motor, brake, and/or transmission is selected, in part, based on the maximum dynamic torque. The speed and torque (e.g., dynamic and static torque) as needed for each joint indicates the power needed for that joint. For motor, brake and transmission sizing, the dynamic torques for each joint may be combined with partial static torques for each joint, respectively. Due to the use of the virtual trajectory, the dynamic torques are determined in a way decoupled from change in pose of the surgical robot system 100 or robot arm 122. The total torque, including the maximum dynamic torque, is used to size the joints (i.e., transmission, brake, and/or motor) of the robot arm 122.

Figure 10:
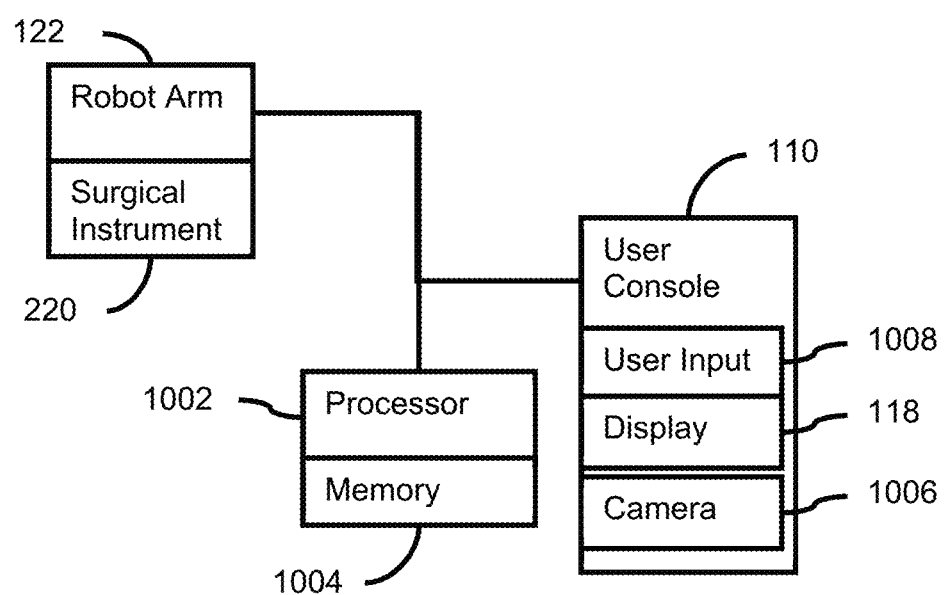
FIG. 10 is a block diagram of one embodiment of a robotic sizing system.

FIG. 10 shows a block diagram of one embodiment of a robot sizing system. The system performs one or any combination of two or more approaches for determining dynamic torque for the robot arm 122. In one approach, user data from tracing a pattern guide may be gathered using the camera 1006 to determine a relationship between velocity and acceleration. In another approach, a synthetic trajectory is formed from the user data from tracing or user data from control of the robot arm 122. In yet another approach, a virtual trajectory is defined and used instead of the synthetic or an actual trajectory.

The sizing system represents or includes a surgical robot system including one or more robot arms 122 with corresponding surgical instruments 202 or other types of instruments connected with the robot arms 122, a processor 1002, and a memory 1004. The user counsel 110 is represented or included as part of the surgical robot system. Additional, different, or fewer components may be provided. For example, the robot arm 122, surgical instrument 220, and/or user counsel 110 are not provided.

The robotic arms 122 each include one or more links and joints. The joints may be pitch or roll joints. A tool drive (e.g., end effector) and cannula for receiving and guiding a surgical tool may be provided on each of the robotic arms 122. Different combinations of links and joints may define or form different parts of the robotic arms 122, such as different parts having different degrees of movement (e.g., translation and/or rotation). Any now known or later develop robotic arm 122 with motors, sensors, links, joints, controllers, and/or other structure may be used.

One or more robotic arms are provided. For example, three or four robotic arms 122 are provided. The robotic arms 122 mount to a table, such as a base of an operating table. Alternatively, cart, floor, ceiling, or other mounts may be used. The robotic arms 122 include a cable or wireless transceiver for communication with the processor 206 or an intermediary (e.g., control tower 130).

The robotic surgical instruments 202 are one or more graspers, retractors, scalpels, endoscopes, staplers, scissors, or other surgical device for manipulating tissue of the patient. The tissue manipulation may be direct, such as cutting or grasping. The tissue manipulation may be indirect, such as an endoscope pressing or contacting tissue as guided to image or view an interior portion of the patient. Different or the same type of instruments 202 may be mounted to different ones of the robot arms 122. For example, two robot arms 122 may have graspers, a third robot arm 122 may have a scalpel, and a fourth robot arm 122 may have an endoscope.

The robotic surgical instruments 202 connect to the distal ends of the robot arms 122 but may connect at other locations. The connection provides a drive so that the tool may be operated, such as closing a grasper or scissors.

The user counsel 110 is a graphics user interface for interaction of the surgeon with the surgical robot system, such as with a processor for controlling the robotic arms 122. The user interface includes a user input 1008 and a display 118. The user input 1008 and/or the display 118 are provided at the user console 110 and/or control tower 130 but may be at other locations.

The user input 1008 is a button, a keyboard, a rocker, a joy stick, a trackball, a voice recognition circuit, a mouse, a touch pad, a touch screen, sliders, switches, UID 116, foot pedal 114, combinations thereof, or any other input device for inputting to the surgical robot. The display 118 is a monitor, liquid crystal display (LCD), projector, plasma display, CRT, printer, or other now known or later developed device for outputting visual information. In an alternative embodiment, the display 118 is a head mounted display. The user input 1008 may be a sensor or sensors for detecting eye movement and/or blinking. In yet other embodiments, the user input 1008 is a microphone for voice-based input. A speaker for output of audio information may be provided instead of or in addition to the display 118.

The camera 1006 is a digital camera for optical tracking of user motion, such as tracking during use of the UID 116 to control the robot arm 122 or trace a target. The camera 1006 may be a stereo camera and/or depth camera in some embodiments. The camera 1006 is positioned relative to a user and a target pattern or user counsel 110 for tracking human motion in tracing the target pattern or controlling the robot arm 122 with the user input 1008.

The processor 1002 is a computer that drives and/or models the robotic arms 122 and/or surgical instruments 202. The processor 1002 is a general processor, central processing unit, control processor, graphics processor, graphics processing unit, digital signal processor, application specific integrated circuit, field programmable gate array, digital circuit, analog circuit, artificial intelligence processor, combinations thereof, or other now known or later developed device for sizing joints of the robot arm 122. The processor 1002 is a single device or multiple devices operating in serial, parallel, or separately. The processor 1002 may be a main processor of a computer, such as a laptop, server, workstation, or desktop computer, or may be a processor for handling some tasks in a larger system. Based on hardware, software, firmware, or combinations thereof, the processor 1002 is configured to implement instructions or perform acts.

The processor 1002 is configured to implement the acts of FIGS. 3, 6, and/or 8. The processor 1002 is configured to determine a relationship between velocity and acceleration based on tracking human tracing of a pattern guide at the user counsel 110 using the camera 1006. The processor 1002 is configured to determine velocity and acceleration vector or directions by generating a synthetic trajectory based on user input from a population of users. The processor 1002 is configured to determine velocity and acceleration vector or directions by defining the directions as a virtual vector. The processor 1002 is configured to determine dynamic torque from pose, velocity vector, and acceleration vector.

The memory 1004 or another memory is a non-transitory computer readable storage medium storing data representing instructions executable by the programmed processor 1002. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

Instructions are provided for any of the acts discussed herein. The instructions are for sizing, such as for design and/or testing of a surgical robot. The instructions are for generating a relationship between velocity and acceleration, generating a synthetic trajectory, and/or generating a virtual trajectory.

Provided below are representative claiming embodiments for the synthetic trajectory (A) and the virtual trajectory (B):

A1. A method for testing a surgical robotic system, the method comprising:
obtaining user data representing input of movement control over a plurality of trajectories from a plurality of users;
generating a synthetic trajectory optimized to the user data, the synthetic trajectory indicating a time history of a state of the robotic surgical system;
analyzing the surgical robotic system using inverse kinematics and inverse dynamics from instantaneous output from the synthetic trajectory; and
verifying performance of the surgical robotic system from the analyzing.

A2. The method of claim 1 wherein obtaining the user data comprises obtaining with each of the users generating the user data for different rates of the movement control with an untethered freehand controller, the trajectories comprising first trajectories for a first rate of the different rates and second trajectories for a second rate of the different rates.

A3. The method of claim 1 wherein obtaining the user data comprises obtaining the user data representing input to trace a target with an untethered freehand controller.

A4. The method of claim 1 wherein generating comprises optimizing the synthetic trajectory to exhibit one or more characteristics matched to the user data without being an actual trajectory represented by the user data, the characteristics comprising frequency, velocity, and acceleration.

A5. The method of claim 4 wherein optimizing comprises optimizing with a cost function including terms for the characteristics, the frequency comprising a primary frequency and a secondary frequency, the velocity comprising a maximum velocity, and the acceleration comprising a maximum acceleration.

A6. The method of claim 1 wherein generating comprises generating the synthetic trajectory as an orbital-type trajectory parameterized by radius, orbital frequency, equatorial precession frequency, perturbation of the radius, and perturbation frequency.

A7. The method of claim 6 wherein generating comprises generating the synthetic trajectory as having a high-coverage distribution of linear acceleration directions.

A8. The method of claim 1 wherein analyzing comprises testing by modeling operation of the robotic surgical system moving along the synthetic trajectory.

A9. The method of claim 1 wherein analyzing comprises determining a torque or power from the instantaneous output being the state of the robotic surgical system from the synthetic trajectory at a given time.

A10. The method of claim 1 wherein analyzing comprises calculating torque at a joint of the robotic surgical system using an instantaneous output of the synthetic trajectory and determining motor power from the torque.

A11. The method of claim 1 wherein verifying comprises verifying a transmission and/or motor of the surgical robot system as capable of operation in the synthetic trajectory.

A12. A non-transitory computer readable storage medium having stored therein data representing instructions executable by a programmed processor for design or testing of a surgical robot, the storage medium comprising instructions for:
fitting first parameters of a synthetic trajectory to a first frequency, a first velocity, and/or a first acceleration from user input to control the surgical robot;
generating a second velocity and/or a second acceleration by the synthetic trajectory with the first parameters as fit to the first frequency, the first velocity, and/or the first acceleration; and determining dynamic torque for a motor of the surgical robot from the second velocity and/or second acceleration.

A13. The non-transitory computer readable storage medium of claim 12 wherein fitting comprises fitting an orbital-type trajectory parameterized by radius, orbital frequency, equatorial precession frequency, perturbation of the radius, and perturbation frequency fit to the first frequency, the first velocity, and the first acceleration.

A14. The non-transitory computer readable storage medium of claim 13 wherein fitting comprises fitting with the orbital trajectory such that the synthetic trajectory has an high-coverage distribution of linear acceleration directions.

A15. The non-transitory computer readable storage medium of claim 13 wherein fitting comprises fitting the synthetic trajectory as different than a user entered trajectory, the synthetic trajectory fit to the first frequency, the first velocity, and the first acceleration derived from a plurality of user inputs from different users.

A16. The non-transitory computer readable storage medium of claim 13 wherein generating comprises generating the second velocity and/or second acceleration as an instantaneous state of the surgical robot from the synthetic trajectory at a time, and wherein determining the torque comprises determining the dynamic torque with inverse dynamics from the instantaneous state.

A17. The non-transitory computer readable storage medium of claim 13 further comprising selecting a motor for the surgical robot based on the dynamic torque.

A18. The non-transitory computer readable storage medium of claim 13 further comprising testing the surgical robot based on the dynamic torque.

B1. A method for generating a quasi-trajectory of a surgical robotic system, the method comprising:

defining a plurality of well-spaced directions for velocity and acceleration at each of a plurality of poses of the surgical robotic system;

determining dynamic torque of the surgical robotic system for each vector combination of the directions for the velocity and the acceleration at each of the poses of the surgical robotic system; and selecting a motor of the surgical robotic system based on a maximum one of the dynamic torques over the poses.

B2. The method of claim 1 wherein defining comprises defining ten or more of the directions in three spatial dimensions, the defining providing 100 or more vector combinations for the directions for the velocity and the acceleration.

B3. The method of claim 1 wherein defining comprises defining free of consideration of a trajectory of the surgical robotic system.

B4. The method of claim 1 wherein defining comprises defining decoupled from time, and wherein determining the dynamic torque for each vector combination comprises determining decoupled from change in the pose of the surgical robotic system.

B5. The method of claim 1 wherein defining comprises defining with the poses comprising a plurality of different surgical poses of the surgical robot.

B6. The method of claim 1 wherein determining the dynamic torque comprises determining with inverse dynamics.

B7. The method of claim 1 wherein the vector combinations of the velocity and acceleration are in a task space for operation of the surgical robotic system, further comprising converting the vector combinations of the velocity and acceleration into a velocity and an acceleration in joint space for joints of the surgical robotic system, and wherein determining the dynamic torque comprises determining the dynamic torque in the joint space.

B8. The method of claim 7 wherein the vector combinations of the velocity and acceleration are for an end effector of the surgical robotic system, and wherein determining the dynamic torques comprises determining for each of a plurality of the joints of the surgical robotic system.

B9. The method of claim 1 further comprising determining acceleration from a curve fit to statistical data from tracings of a target by multiple users, and wherein determining the torque comprises determining as a function of the acceleration.

B10. A non-transitory computer readable storage medium having stored therein data representing instructions executable by a programmed processor for trajectory representation in a surgical robot, the storage medium comprising instructions for:

sampling a high-coverage spatial distribution of vector combinations of velocity and acceleration for each of a plurality of poses of the surgical robot;

determining dynamic torque of the surgical robotic system for each of the vector combinations at each of the poses of the surgical robotic system; and identifying a maximum of the dynamic torques.

B11. The non-transitory computer readable storage medium of claim 10 wherein sampling comprises sampling over at least 200 vector combinations with evenly spaced angles about a point on the surgical robot for each of the poses.

B12. The non-transitory computer readable storage medium of claim 10 wherein sampling comprises sampling without reference to a trajectory of the surgical robotic system and wherein determining comprises determining with inverse dynamics without a change in time.

B13. The non-transitory computer readable storage medium of claim 10 further comprising an instruction for converting the velocities and accelerations from a frame of reference for an end effector to a frame of reference for joints of the surgical robot.

B14. The non-transitory computer readable storage medium of claim 10 further comprising instructions for determining acceleration from a curve fit to statistical data from tracings of a target by multiple users, and wherein determining the dynamic torque comprises determining as a function of the acceleration.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for parameterizing human motion in a surgical robotic system, the method comprising:

positioning a pattern guide at a surgeon console of the surgical robotic system;

tracking motions of a plurality of users tracing the pattern guide in conditions for two different speeds of the tracing;

determining an individual high speed and individual high acceleration for the motions of each of the users for each of the conditions;

determining a population high speed and population high acceleration from the individual high speeds and individual high accelerations for the motions of the users for each of the conditions;

fitting a curve to the population high speed and population high acceleration for the conditions;

calculating a maximum acceleration from the curve given a maximum speed; and determining a dynamic torque for a motor of the surgical robot from the maximum speed and the maximum acceleration.

2. The method of claim 1 wherein positioning comprises positioning the pattern guide comprising a circle around a cross hairs, and wherein tracking the motions comprises tracking the motions around the circle and along each of the cross hairs.

3. The method of claim 1 wherein tracking the motions comprises tracking an optical marker held by the users with a camera.

4. The method of claim 1 wherein tracking comprises tracking with the two different speeds comprising tracing in an accurate condition and tracing in a fast condition, and further comprising tracking at a third speed in a probable condition between the accurate condition and the fast condition;

wherein fitting comprises fitting the curve for the accurate, probable, and fast conditions.

5. The method of claim 1 wherein determining the individual high speed and the individual high acceleration comprises determining the individual high speed and the individual high acceleration as a mean speed plus 3 sigma and as a mean acceleration plus 3 sigma, respectively, from the motions of each of the users, and wherein determining the population high speed and population high acceleration comprises determining a mean of the individual high speeds plus 1 sigma and a mean of the individual high accelerations plus 1 sigma, respectively.

6. The method of claim 1 further comprising determining individual mean speed, individual mean acceleration, and two individual peak frequencies for the motions of each of the users, and determining population mean speed, population mean acceleration, and two population peak frequencies from the individual mean speeds, individual mean accelerations, and two individual peak frequencies for the motions of the users.

7. The method of claim 1 wherein fitting the curve comprises fitting the curve to points for each of the conditions, the points comprising the population high speed and population the high acceleration, and fitting the curve to a zero speed and zero acceleration as an additional point.

8. The method of claim 1 wherein determining the dynamic torque comprises determining from a synthetic trajectory optimized using the maximum acceleration.

9. The method of claim 1 wherein determining the dynamic torque comprises performing inverse dynamic calculations at arbitrary directions for the maximum speed and the maximum acceleration at a pose of the surgical robot.

10. A non-transitory computer readable storage medium having stored therein data representing instructions executable by a programmed processor for design or testing of a surgical robot, the storage medium comprising instructions for:

determining statistical data from samples of surgical robot control under different operating environments for a population of users;

generating a relationship of velocity to acceleration for the surgical robot control over the different operating environments; and determining dynamic torque for the surgical robot from an acceleration determined from the relationship given a velocity of the surgical robot.

11. The non-transitory computer readable storage medium of claim 10 wherein determining the statistical data comprises determining individual velocity and individual acceleration for each of the users tracing a target and determining the statistical data as population velocity and population acceleration from the individual velocities and individual accelerations.

12. The non-transitory computer readable storage medium of claim 10 wherein determining the statistical data comprises determining with the different operating environments comprising control over a range of three or more balances in control between speed and accuracy.

13. The non-transitory computer readable storage medium of claim 10 wherein generating the relationship comprises fitting a curve from zero velocity and zero acceleration through points corresponding to the velocity and the acceleration in each of the different operating environments.

14. The non-transitory computer readable storage medium of claim 10 wherein determining the dynamic torque comprises determining with inverse dynamics.

15. The non-transitory computer readable storage medium of claim 10 wherein determining the dynamic torque comprises determining from a synthetic trajectory optimized using the acceleration.

16. The non-transitory computer readable storage medium of claim 10 wherein determining the dynamic torque comprises performing inverse dynamic calculations at arbitrary directions for the velocity and the acceleration at a pose of the surgical robot.

* * * * *